US011786563B2

(12) United States Patent
Krishnan et al.

(10) Patent No.: US 11,786,563 B2
(45) Date of Patent: *Oct. 17, 2023

(54) SPORE-BASED PROBIOTIC COMPOSITION FOR MODULATION OF DERMAL AND SUB-DERMAL PROPERTIES

(71) Applicant: Novozymes A/S, Bagsvaerd (DK)

(72) Inventors: Kiran Krishnan, Saint Augustine, FL (US); Dale M. Kriz, Saint Augustine, FL (US); Thomas F. Bayne, Saint Augustine, FL (US)

(73) Assignee: Novozymes A/S, Bagsvaerd (DK)

( * ) Notice: Subject to any disclaimer, the term of this patent is extended or adjusted under 35 U.S.C. 154(b) by 102 days.

This patent is subject to a terminal disclaimer.

(21) Appl. No.: 17/468,485

(22) Filed: Sep. 7, 2021

(65) Prior Publication Data

US 2021/0401901 A1    Dec. 30, 2021

Related U.S. Application Data

(63) Continuation of application No. 16/743,186, filed on Jan. 15, 2020, now Pat. No. 11,129,860.

(60) Provisional application No. 62/900,023, filed on Sep. 13, 2019, provisional application No. 62/792,719, filed on Jan. 15, 2019.

(51) Int. Cl.
    | | |
    |---|---|
    | *C12N 1/20* | (2006.01) |
    | *A61K 35/742* | (2015.01) |
    | *A23L 33/135* | (2016.01) |
    | *A23L 33/00* | (2016.01) |
    | *A61P 17/10* | (2006.01) |
    | *A61K 9/00* | (2006.01) |

(52) U.S. Cl.
    CPC .......... *A61K 35/742* (2013.01); *A23L 33/135* (2016.08); *A23L 33/40* (2016.08); *A61K 9/0053* (2013.01); *A61P 17/10* (2018.01); *A23V 2002/00* (2013.01)

(58) Field of Classification Search
    CPC ....................................................... C12N 1/20
    See application file for complete search history.

(56) References Cited

U.S. PATENT DOCUMENTS

2015/0079040 A1    3/2015    O'neill et al.
2018/0289752 A1    10/2018   Krishnan et al.

FOREIGN PATENT DOCUMENTS

CN    104582712 A    4/2015
WO    2006117019 A1    11/2006

OTHER PUBLICATIONS

McFarlin et al., "Thirty days of multi-strain probiotic supplementation was associated with reduced incidence of post-prandial dietary endotoxin, triglycerides and disease risk biomarkers," Gastroenterology 152(5, Suppl. 1):S816-817, May 2017.*
Anonymous, 2014, MegaSporeBiotic, Clinicalnutritioncenters, 1-3.
Anonymous, 2016, MegaSporeBiotic, Probiotic and Antioxidant combination,1-2.

(Continued)

*Primary Examiner* — Rosanne Kosson
(74) *Attorney, Agent, or Firm* — David Fazzolare

(57) ABSTRACT

The present invention relates to methods of modulating dermal and sub-dermal properties of a subject. The present invention relates to methods comprising administering to a subject a spore-based probiotic composition.

18 Claims, 10 Drawing Sheets

Specification includes a Sequence Listing.

(56) References Cited

OTHER PUBLICATIONS

Brian, 2017, The American Journal of Gastroenterology, S657-S658.
Gastrointestinal, 2017, World Journal of Contents,100-149.
Notay et al., 2017, Am J Clin Dermatol 18, 721-732.
Trivedi et al., 2018, American journal of clinical dermatology 19, 505-516.
Foolad et al., 2015, Dermatology online journal 21(6), 2.
Walters et al., 2015, Novel Systems Biology Techniques 1(1), 1-10.
Lui, Y., et al., 2018, Nutrients, 10 (1537), 1-19.
Diaz, et al., 2017, Nutrients, 9 f(555), 1-19.
Microbiomelabs, "MegaSporeBiotics", Nov. 2, 2017 (Nov. 2, 2017), retrieved on Mar. 18, 2020 from https://microbiomelabs.com/shop/megasporebiotic/; entire document especially para 1.
Anonymous, 2017, MegaSporeBiotic—Microbiome Labs.
Anonymous, 2014, Clinicalnutritioncenters—Megasporebiotic. Clinicalnutrition centers, "MegaSporeBiotic", Feb. 3, 2014 (Feb. 2, 2014), retrieved on Mar. 18, 2020 from https://www.google.com/search?source=hp&ei=2zByXvH7CJDUsAX2967oDg&q=inurl%3Ahttps%3A%2F%2Fwww.clinicalnutritioncenters.com%2Fmegasporebiotic-mega-spore-biotic-by-physicians-exclusive-60-caps%2F&oq=inurl%3Ahttps%3A%2F%2Fwww.clinicalnutritioncenters.com%2Fmegasporebiotic-mega-spore-biotic-by-physicians-exclusive-60-caps%2F&gs_I=psy-ab.3 . . . 1167.8234..8827 . . . 0.0..0.0.0 . . . . . . . . 1 . . . . 211..gws-wiz.0nBQWnOLRE&ved=0ahUKEwix1e_PnqToAhUQKqwKHfa7C-0Q4UDCAg&uact=5&as_qdr=y15; entire document, especially p. 2 supplemental facts, p. 2 para. 1—Continuation of cited reference in previous box above, line 1.
McFarlin et al., World journal of Gastrointestinal Pathophysiology, 2017, 117-126, 8(3).

\* cited by examiner

```
                        SEQUENCE LISTING

<160> NUMBER OF SEQ ID NOS: 2

<210> SEQ ID NO 1
<211> LENGTH: 33
<212> TYPE: DNA
<213> ORGANISM: artificial sequence
<220> FEATURE:
<223> OTHER INFORMATION: synthetic

<400> SEQUENCE: 1
tcgtcggcag cgtcagatgt gtataagaga cag                                33

<210> SEQ ID NO 2
<211> LENGTH: 34
<212> TYPE: DNA
<213> ORGANISM: artificial sequence
<220> FEATURE:
<223> OTHER INFORMATION: synthetic

<400> SEQUENCE: 2
gtctcgtggg ctcggagatg tgtataagag acag                               34
```

SPORE-BASED PROBIOTIC COMPOSITION FOR MODULATION OF DERMAL AND SUB-DERMAL PROPERTIES

CROSS-REFERENCE TO RELATED APPLICATIONS

This application is a Continuation of U.S. application Ser. No. 16/743,186, filed Jan. 15, 2020, now U.S. Pat. No. 11,129,860, which claims the benefit of U.S. Provisional application No. 62/792,719, filed on Jan. 15, 2019 and U.S. Provisional application No. 62/900,023, filed on Sep. 13, 2019, each of which are hereby incorporated by reference herein.

TECHNICAL FIELD

The present disclosure relates to the field of spore-based probiotic compositions. A spore-based probiotic composition is provided that comprises at least one viable probiotic microorganism having a biological or therapeutic activity on the hypodermis, dermis, and/or epidermis. Also provided are methods of producing spore-based probiotic compositions.

BACKGROUND

The microbiome is the genetic material of all microbes (bacteria, fungi, protozoa, and viruses) that live on or in the human body. Microbes outnumber human cells in a 10:1 ratio. Most microbes live in the gut, particularly the large intestine. The number of genes of all microbes in the microbiome is 200-fold that of the human genome. The microbiome may weigh as much as 2 kg. The bacteria help digest food, regulate the immune system, protect against other bacteria that cause disease, and produce vitamins (including the B vitamins B12, thiamine, and riboflavin; and Vitamin K, which is required for blood coagulation). The microbiome became generally recognized in the late 1990s. See, e.g., Marilyn Hair & Jon Sharpe, *Fast facts about the human microbiome*, CTR. FOR ECOGENETICS & ENVTL. HEALTH, UNIV. WASHINGTON (2014), incorporated by reference herein in its entirety.

The microbiome is essential for human development, immunity, and nutrition. Bacteria living in and on humans are not invaders but, rather, beneficial colonizers. Autoimmune diseases including diabetes, rheumatoid arthritis, muscular dystrophy, multiple sclerosis, and fibromyalgia are associated with dysfunctional microbiomes. Disease-causing microbes accumulate over time and change genetic activities and metabolic processes, triggering abnormal immune responses against substances and tissues that are, in fact, part of a healthy body. Autoimmune diseases appear to run in families not because of germline inheritance but, rather, by inheritance of the familial microbiome. See, e.g., Hair & Sharpe, 2014.

Humans are essentially sterile during gestation. During and after birth, however, every bodily surface, including the skin, mouth, and gut, becomes host to an enormous variety of microbes: bacterial, archaeal, fungal, and viral. Under normal circumstances, the microbes aid in food digestion and maintenance of immune systems; dysfunctional human microbiotas have been linked to conditions ranging from inflammatory bowel disease to antibiotic-resistant infections. See, e.g., X. C. Morgan & C. Huttenhower, *Chapter 12: human microbiome analysis*, 8 PLoS COMPUTATIONAL BIOLOGY e1002808 (2012), incorporated by reference herein in its entirety.

The gut microbiota is essential to human health throughout life. The gut microbiome is a vast collection of bacteria, viruses, fungi, and protozoa that colonize the gastrointestinal tract and outnumber human cells 10-fold. Exposures in early life [Mode of delivery (maternal microbes); infant diet (selective substrates); antibiotics (selective killing); probiotics (selective enrichment); and physical environment (environmental microbes)] results in colonization of gut microbiota which contributes to the development of the immune system, intestinal homeostasis and host metabolism. Disruption of the gut microbiota is associated with a growing number of diseases. See, e.g., M. B. Azad, et al., *Gut microbiota of healthy Canadian infants: profiles by mode of delivery and infant diet at 4 months*, 185 CAN. MED. ASS'N J. 385 (2013), incorporated by reference herein in its entirety. Recent advances in metagenomics have enhanced our understanding of the gut microbiome, suggesting that it can provide important immune and metabolic benefits to humans.

Interestingly, the intestinal microbiota affects the immune and/or inflammatory status of the host by modulating intestinal barrier function and by influencing the development of the immune response. The gut microbiome's influence on the human immune system is far-reaching and intricately designed to enable immune tolerance of dietary and environmental antigens and provide protection against potential pathogens and toxins. Several gut microbial structures that play an important role in barrier functions have been identified. The secreted protein, p40, from Lactobacilli LGG ameliorates cytokine-mediated apoptosis and disruption of the gut epithelial barrier, and flagellin from *Escherichia coli* Nissle is associated with induction of β-defensin 2 in epithelial cells. See, e.g., F. Yan, et al., *Colon-specific delivery of a probiotic-derived soluble protein ameliorates intestinal inflammation in mice through an EGFR-dependent mechanism*, 121 J. CLINICAL INVESTIGATION 2242 (2011); M. Schlee, et al., *Induction of human beta-defensin 2 by the probiotic Escherichia coli Nissle 1917 is mediated through flagellin*, 75 INFECTION & IMMUNITY 2399 (2007); each of which is incorporated by reference herein in its entirety. Gut microbiota has been shown to direct maturation of the host immune system, to play a key role in the induction of immunoglobulin ("Ig") A and germinal centers, and to drive Th1, Th17, and regulatory T cell ("Treg") development in the gut. See, e.g., S. K. Mazmanian, et al., *An immunomodulatory molecule of symbiotic bacteria directs maturation of the host immune system*, 122 CELL 107 (2005); H. L. Klaasen, et al., *Intestinal, segmented, filamentous bacteria in a wide range of vertebrate species*, 27 LABANIMAL 141 (1993); G. L. Talham, et al., *Segmented filamentous bacteria are potent stimuli of a physiologically normal state of the murine gut mucosal immune system*, 67 INFECTION & IMMUNITY 1992 (1999); H. Bauer, et al., *The response of the lymphatic tissue to the microbial flora. Studies on germfree mice*, 42 AM. J. PATHOLOGY 471 (1963); K. Atarashi, et al., *Induction of colonic regulatory T cells by indigenous Clostridium species*, 331 SCIENCE 337 (2011); V. Gaboriau-Routhiau, et al., *The key role of segmented filamentous bacteria in the coordinated maturation of gut helper T cell responses*, 31 IMMUNITY 677 (2009); I. I. Ivanov, et al., *Induction of intestinal Th17 cells by segmented filamentous bacteria*, 139 CELL 485 (2009); each of which is incorporated by reference herein in its entirety. In most individuals, the commensal-mediated induction of these different components of the immune response is beneficial for host health. However, the composition of the gut microbiota can differentially influence various immune cell populations and adversely affect autoimmune/inflammatory disease-susceptible hosts, e.g., the presence of segmented filamentous bacteria ("SFB") has been associated with a strong Th17 response and development of Th17-mediated diseases. See, e.g., Y. K. Lee, et al., *Proinflammatory T-cell responses to gut microbiota promote experimental autoimmune encephalomyelitis,* 108 (Suppl. 1) PROCEEDINGS NAT'L ACAD. SCI. USA 4615 (2011); R. Stepankova, et al., *Segmented filamentous bacteria in a defined bacterial cocktail induce intestinal inflammation in SCID mice reconstituted with CD45RBhigh CD4+ T cells,* 13 INFLAMMATORY BOWEL DISEASES 1202 (2007); H. J. Wu, et al., *Gut-residing segmented filamentous bacteria drive autoimmune arthritis via T helper 17 cells,* 32 IMMUNITY 815 (2010); each of which incorporated by reference herein in its entirety.

Interestingly, the gut microbiome and skin are uniquely connected in purpose and function. As the primary interface with the external environment, both organs are crucial in maintaining overall homeostasis. Recent research has demonstrated a strong bidirectional connection between the gut and skin, suggesting that digestive health plays a pivotal role in skin homeostasis and allostasis. Gut bacteria have been shown to participate in the pathophysiology of many inflammatory disorders, including skin disorders such as acne, atopic dermatitis ("AD"), scleroderma, vitiligo, rosacea, and psoriasis.

Skin and mucosal surfaces of mammalian species are populated by millions of bacteria that impart diverse metabolic effects. See, e.g., J. K. Nicolson, et al., *Host-gut microbiota metabolic interactions,* 336 SCIENCE 1262 (2012), incorporated by reference herein in its entirety. These host-associated microbes play a well-established role in homeostasis in the gastrointestinal ("GI") tract. See, e.g., Y. K. Lee & S. K. Mazmanian, *Has the microbiota played a critical role in the evolution of the adaptive immune system?,* 330 SCIENCE 1768 (2010); N. P. McNulty, et al., *The impact of a consortium of fermented milk strains on the gut microbiome of gnotobiotic mice and monozygotic twins,* 3 SCI. TRANSLATIONAL MEDICINE 106ra106; each of which is incorporated by reference herein in its entirety. There is now substantial evidence linking various gut microbiota and local immunity networks with systematic effects on the immune system. See, e.g., T. Chinen & A. Y. Rudensky, *The effects of commensal microbiota on immune cell subsets and inflammatory responses,* 245 IMMUNOLOGICAL REVIEWS 45 (2012); L. V. Hooper, et al., *Interactions between the microbiota and the immune system,* 336 SCIENCE 1268 (2012); C. L. Maynard, et al., *Reciprocal interactions of the intestinal microbiota and immune system,* 489 NATURE 231 (2012); each of which is incorporated by reference herein in its entirety. Disruption of the normal balance between microbial communities in the intestine is associated with allergic, autoimmune, metabolic, and neoplastic pathologies in the GI tract and other distant tissues. See, e.g., K. E. Fujimura, et al., *Role of the gut microbiota in defining human health,* 8 EXPERT REVIEW OF ANTI-INFECTIVE THERAPY 435 (2010); A. S. Neish, *Microbes in gastrointestinal health and disease,* 136 GASTROENTEROLOGY 65 (2009); J. C. Clemente, et al., *The impact of the gut microbiota on human health: an integrative view,* 148 CELL 1258 (2012); M. C. Noverr & G. B. Huffnagle, *Does the microbiota regulate immune responses outside the gut?,* 12 TRENDS IN MICROBIOLOGY 562 (2004); H. Tlaskalova-Hogenova, et al., *The role of gut microbiota (commensal bacteria) and the mucosal barrier in the pathogenesis of inflammatory and autoimmune diseases and cancer: contribution of germ-free and gnotobiotic animal models of human diseases,* 8 CELLULAR & MOLECULAR IMMUNOLOGY 110 (2011); each of which is incorporated by reference herein in its entirety. Along these lines, experimental and clinical studies have shown that the dietary enrichment with certain "probiotic" organisms activates immune and metabolic pathways that restore tissue homeostasis and promote overall health. See, e.g., J. Ravel, et al., *Vaginal microbiome of reproductive-age women,* 108 (Suppl. 1) PROCEEDINGS NAT'L ACAD. SCI. USA 4680 (2011); A. A. Litonjua & S. T. Weiss, *Is vitamin D deficiency to blame for the asthma epidemic?,* 120 J. ALLERGY & CLINICAL IMMUNOLOGY 1031 (2007); M. H. Floch, et al., *Recommendations for probiotic use-2011 update,* 45 (Suppl.) J. CLINICAL GASTROENTEROLOGY S168 (2011); each of which is incorporated by reference herein in its entirety.

Probiotics are most commonly defined as "live microorganisms which when administered in adequate amounts confer a health benefit on the host," such as restoring or improving the composition of intestinal microflora. See, e.g., FAO/WHO, *Guidelines for the evaluation of probiotics in food,* London, Ontario, Canada (2002), incorporated by reference herein in its entirety. Probiotics are typically provided as dietary supplements containing potentially beneficial bacteria or yeast and are widely consumed in foods, including dairy products and probiotic fortified foods, as well as in capsules, tablets, and powders. See, e.g., C. Stanton, et al., *Market potential of probiotics,* 73 (Suppl.) AM. J. CLINICAL NUTRITION 476S (2001), incorporated by reference herein in its entirety. It is believed by many experts that the ideal probiotic should remain viable at the level of the intestine and should adhere to the intestinal epithelium to confer a significant health benefit. There is some evidence to support the importance of viability in human studies, with viable bacteria having greater immunological effects that nonviable bacteria. See, e.g., M. Kaila, et al., *Viable versus inactivated lactobacillus strain GG in acute rotavirus diarrhea,* 72 ARCHIVES OF DISEASE IN CHILDHOOD 51 (1995); P. V. Kirjavainen, et al., *Probiotic bacteria in the management of atopic disease: underscoring the importance of viability,* 36 J. PEDIATRIC GASTROENTEROLOGY & NUTRITION 223 (2003); each of which is incorporated by reference herein in its entirety. Some of the best characterized probiotics have also been shown to adhere strongly to intestinal epithelium in both in vitro and in vivo studies. See, e.g., M. Alander, et al., *Persistence of colonization of human colonic mucosa by a probiotic strain, Lactobacillus rhamnosus GG, after oral consumption,* 65 APPLIED & ENVIRONMENTAL MICROBIOLOGY 351 (1999), incorporated by reference herein in its entirety. Probiotics must also be resistant to gastric acid digestion and to bile salts to reach the intestine intact, and they should be nonpathogenic. Most probiotics are strains of lactic acid bacteria, including *Lactobacillus* and *Bifidobacterium* species. Some have been isolated from the intestinal microbiota of healthy humans; others have been isolated from fermented dairy products. Species and strains from other bacterial genera such as *Streptococcus, Bacillus, Enterococcus, Lactococcus, Propionibacterium, Saccharomyces,* and *Escherichia* have also been used as probiotics or have been reported to have probiotic properties, but there are concerns surrounding the safety of some of these probiotics because they contain many pathogenic species, particularly within the genus *Enterococcus*. Nonbacterial microorganisms such as yeasts from the genus *Saccharomyces* have also been used as probiotics for many years.

An exaggerated paradigm of an organ distal from the bowel that could benefit from probiotic consumption is the skin. Interestingly, research data from both mice and humans suggest that dietary supplementation with probiotic lactic acid bacteria has beneficial effects in the skin. See, e.g., M. H. Floch, et al., 2011; P. Arck, et al., *Is there a 'gut-brain-skin axis'?*, 19 EXPERIMENTAL DERMATOLOGY 401 (2010); L. Chapat, et al., *Lactobacillus casei reduces CD8+ T cell-mediated skin inflammation*, 34 EUR. J. IMMUNOLOGY 2520 (2004); A. Gueniche, et al., *Supplementation with oral probiotic bacteria maintains cutaneous immune homeostasis after UV exposure*, 16 EUR. J. DERMATOLOGY 511 (2006); J. Krutmann, *Pre- and probiotics for human skin*, 54 J. DERMATOLOGICAL SCI. 1 (2009); each of which is incorporated by reference herein in its entirety. The importance of probiotic effects on skin extends beyond obvious cosmetic aspects to broader host health. Indeed, the appearance of the skin and its appendages has been considered by medicine traditions worldwide as a clinical sign of good health.

In a previous GI immune-related study, changes in fur appearance have been documented in mice treated with probiotics. Similar "probiotic" organisms dominate under natural conditions during infancy and fertility in many animal species. See, e.g., K. E. Fujimura, et al., 2010; A. S. Neish, 2009; J. C. Clemente, et al., 2012. Daily consumption of *Lactobacillus reuteri*, a human microbial isolate proven effective at suppressing colitis, added to drinking water was found to lead to lustrous fur similar to that seen in mice eating probiotic yogurt. See, e.g., D. M. Saulnier, et al., *Exploring metabolic pathway reconstruction and genome-wide expression profiling in Lactobacillus reuteri to define functional probiotic features*, 6 PLoS ONE e18783 (2011), incorporated by reference herein in its entirety. Probiotic bacteria have been hypothesized to impart integumentary health benefits by an anti-inflammatory mechanism as previously characterized in GI tract mucosa and in skin. See, e.g., C. Di Giacinto, et al., *Probiotics ameliorate recurrent Th1-mediated murine colitis by inducing IL-10 and IL-10-dependent TGF-beta-bearing regulatory cells*, 174 J. IMMUNOLOGY 3237 (2005); D. H. Suh, et al., *Changes of comedonal cytokines and sebum secretion after UV irradiation in acne patients*, 12 EUR. J. DERMATOLOGY 139 (2002); each of which is incorporated by reference herein in its entirety.

Probiotic-induced differences in hair luster in female mice emerged rapidly after feeding yogurt or purified bacteria, leading to postulation that immediate impact on hair gloss may be due to increased epithelial sebaceous secretions. See, e.g., J. A. Eurell & B. Frappier, 405 DELLMAN'S TEXTBOOK OF PHYSICAL HISTOLOGY (Shigeto Yamashiro, ed., Blackwell Publ'g 2006), incorporated by reference herein in its entirety. Sebum is comprised of fatty acids including wax esters that may simultaneously alter pH and fill imperfections in the hair cuticle enhancing reflection of light. See, e.g., J. B. Cheng & D. W. Russell, *Mammalian wax biosynthesis. II. Expression cloning of wax synthase cDNAs encoding a member of the acyltransferase enzyme family*, 279 J. BIOLOGICAL CHEMISTRY 37798 (2004); A. J. Thody & S. Shuster, *Control and function of sebaceous glands*, 69 PHYSIOLOGICAL REVIEWS 383 (1989); each of which is incorporated by reference herein in its entirety. Excessive sebum excretion is known to increase the risk of developing acne, and many acne medications aim to reduce the sebum excretion rate ("SER") in users. For example, lanolin, a waxy sebaceous secretion in sheep, is frequently used in cosmetics to protect human skin and also impart a healthful glow in this way. Increased sebocyte counts after probiotics were seen in mice of both genders; however, significant acidity and shinier fur were seen only in female animals. More frequently grooming activity arising from elevated levels of oxytocin in our mice after feeding probiotics may help distribute sebum and hasten radiance in probiotic-fed animals. See, e.g., J. A. Amico, et al., *Centrally administered oxytocin elicits exaggerated grooming in oxytocin null mice*, 78 PHARMACOLOGY BIOCHEMISTRY & BEHAVIOR 333 (2004), incorporated by reference herein in its entirety. In contrast with wt animals, female mice deficient in IL-10 exhibited alkaline skin and mucosae and failed to benefit clinically from probiotic supplementation. This matched prior studies showing IL-10-dependent recruitment of anti-inflammatory immune cells after probiotic consumption and supports the relevancy of microbially-induced inflammation in health. During these studies, phenotypic differences between wild type and IL-10-deficient C57BL/6 animals did not emerge until after feeding of probiotic yogurt or *L. reuteri*, leading to the conclusion that IL-10 was specifically required for benefit from probiotic bacteria. Precisely how *L. reuteri* and inflammation coincide mechanistically in this process within the pilosebaceous unit remains to be determined. Probiotics may have systematic effects on many inflammatory cells and cytokines, including IL-10, TGF-β1, IL-17, IL-22, IL-1, TNF-α, and others, which also have been shown to have important roles in skin health and disease, and in hair follicle cycling. See, e.g., F. Hacini-Rachinel, et al., *Oral probiotic control skin inflammation by acting on both effector and regulatory T cells*, 4 PLoS ONE e4903 (2009); A. Cavani, et al., *Th1 and Th22 in skin allergy*, 96 CHEMICAL IMMUNOLOGY & ALLERGY 39 (2012); K. S. Stenn & R. Paus, *Controls of hair follicle cycling*, 81 PHYSIOLOGICAL REVIEWS 449 (2001); each of which is incorporated by reference herein in its entirety.

Hair density has also been associated with peak health and vitality in humans in many cultures. See, e.g., P. E. Wheeler, *The loss of functional body hair in man: the influence of thermal environment, body form and bipedality*, 14 J. HUMAN EVOLUTION 23 (1985); F. Muscarella & M. R. Cunningham, *The evolutionary significance and social perception of male pattern baldness and facial hair*, 17 ETHOLOGY & SOCIOBIOLOGY 99 (1996); each of which is incorporated by reference herein in its entirety. Both hair growth and increased sebocyte formation are strongly regulated by hormones; in particular, the androgenic hormone testosterone normally causes robust hair growth in young males. See, e.g., S. Fimmel, et al., *Inhibition of the androgen receptor by antisense oligonucleotides regulates the biological activity of androgens in SZ95 sebocytes*, 39 HORMONE & METABOLIC RESEARCH 149 (2007); M. Schneiders & R. Pausb, *Sebocytes, multifaceted epithelial cells: Lipid production and holocrine secretion*, 42 INT'L J. BIOCHEMISTRY & CELL BIOLOGY 181 (2010); each of which is incorporated by reference herein in its entirety. Elevated levels of androgen hormones in male mice after feeding probiotics may serve to stimulate sebocytes and associated hair follicles in our probiotic-fed animals. See, e.g., S. M. Liva & R. R. Voskuhl, *Testosterone acts directly on CD4+ T lymphocytes to increase IL-10 production*, 167 J. IMMUNOLOGY 2060 (2001), incorporated by reference herein in its entirety. During normal aging in humans, telogen effluvium develops as a result of testosterone metabolites such that quiescent telogen phase scalp hairs predominate causing thinning hair. See, e.g., J. H. Barth, *Should men still go bald gracefully?*, 355 LANCET 161 (2000), incorporated by reference herein in its entirety. Male pattern baldness is incompletely understood, but is attributed to complex interactions between genetics, hormones and inflammation. See, e.g., A. Rebora, *Pathogenesis of androgenetic alopecia*, 50 J. AM. ACADEMY DERMATOLOGY 777 (2004), incorporated by reference herein in its entirety. Extrapolation from data of mice to humans suggests that excessive inflammation in the form of uncontrolled IL-17A subverts scalp hair growth, and this may be remedied by eating probiotic bacteria such as *L. reuteri*, but interpretation is complicated by disparities in hair on scalp versus other body sites of these species.

Skin hydration, on the other hand, is what gives skin the fresh elasticity that we associate with youthful-looking skin. Increased skin hydration appears to reduce the appearance of wrinkles, balances the skin microbiota, and can also improve blemishes.

Antibiotic therapies are common within dermatology, particularly in the treatment of conditions such as acne vulgaris, rosacea, and hidradenitis suppurativa. However, as antibiotics become more prevalent, so does the potential for antibiotic resistance in *C. acnes* (Dessinioti C., Katsambas A., "*Propionibacterium acnes* and antimicrobial resistance in acne," *Clin. Dermatol.* (2017) 35: 163-7). Long-term antibiotic use can have other consequences such as increased risk for gut dysfunction and antibiotic resistance of pathogenic bacteria (Garrett J., Margolis D., "Impact of Long-Term Antibiotic Use for Acne on Bacterial Ecology and Health Outcomes: A Review of Observational Studies," *Curr. Derm. Rep.* (2012) 1: 23-8).

The gut microbiome has been a growing area of interest in relation to the skin. Specifically, it is thought that gut bacteria can be better understood in order to control for skin conditions by manipulating the gut-skin axis (Salem I., Ramser A., Isham N., et al., "The Gut Microbiome as a Major Regulator of the Gut-Skin Axis," *Front. Microbiol.* (2018) 9: 1459). Previous studies show that the gut microbiome may modulate the immune system and inflammation in skin conditions such as psoriasis (Zakostelska Z., Malkova J., Klimesova K., et al., "Intestinal Microbiota Promotes Psoriasis-Like Skin Inflammation by Enhancing Th17 Response," *PLoS One* (2016) 11: e0159539; Thio H. B., "The Microbiome in Psoriasis and Psoriatic Arthritis: The Skin Perspective," *J. Rheumatol. Suppl.* (2018) 94: 30-1; Scher J., Ubeda C., Artacho A., et al., "Decreased bacterial diversity characterizes the altered gut microbiota in patients with psoriatic arthritis, resembling dysbiosis in inflammatory bowel disease," *Arthritis Rheumatol.* (2015) 67: 128-39), acne (Yan H.-M., Zhao H.-J., Guo D.-Y. et al., "Gut microbiota alterations in moderate to severe acne vulgaris patients," *J. Dermatol.* (2018) 45: 1166-71; Deng Y., Wang H., Zhou J., et al., "Patients with Acne Vulgaris Have a Distinct Gut Microbiota in Comparison with Healthy Controls," *Acta Derm. Venereol.* (2018) 98: 783-90), rosacea (Nam J. H., Yun Y., Kim H. S., et al., "Rosacea and its association with enteral microbiota in Korean females," *Exp. Dermatol.* (2018) 27: 37-42), and atopic dermatitis (Lee S. Y., Lee E., Park Y. M., et al., "Microbiome in the Gut-Skin Axis in Atopic Dermatitis," *Allergy Asthma Immunol. Res.* (2018) 10: 354-62). Accordingly, there has been growing interest in the role of probiotics for modulating the skin. Probiotics have gained interest as an alternative approach to modulating the gut microbiome and have been appear to have anti-inflammatory effects both locally and distally from the gut (Plaza-Diaz J., Ruiz-Ojeda F. J., Vilchez-Padial L. M., et al., "Evidence of the Anti-Inflammatory Effects of Probiotics and Synbiotics in Intestinal Chronic Diseases," *Nutrients* (2017) 9:555; Liu Y., Alookaran J. J., Rhoads J. M., "Probiotics in Autoimmune and Inflammatory Disorders," *Nutrients* (2018) 10:1537; Hacini-Rachinel F., Gheit H., Le Luduec J. B., et al., "Oral probiotic control skin inflammation by acting on both effector and regulatory T cells," *PLoS One* (2009) 4: e4903).

Previous studies support that oral probiotics may be helpful for skin disease. Several studies have shown that studies in atopic dermatitis may show benefit (Notay M., Foolad N., Vaughn A. R., et al., "Probiotics, Prebiotics, and Synbiotics for the Treatment and Prevention of Adult Dermatological Diseases," *Am. J. Clin. Dermatol.* (2017) 18: 721-32). A study in acne showed that a probiotic consisting of a mix of *Lactobacillus acidophilus*, *Lactobacillus delbrueckii* subspecies *bulgaricus*, and *Bifidobacterium bifidum* was shown to be as effective as 100 mg daily minocycline in the treatment of acne (Jung G. W., Tse J. E., Guiha I., et al., "Prospective, randomized, open-label trial comparing the safety, efficacy, and tolerability of an acne treatment regimen with and without a probiotic supplement and minocycline in subjects with mild to moderate acne," *J. Cutan. Med. Surg.* (2013) 17: 114-22). Several studies in mice show that oral supplementation with *Bifidobacterium breve* attenuated UV induced biophysical changes in the skin by reducing UV induced increases in transepidermal water loss (TEWL) and decreases in skin hydration (Satoh T., Murata M., Iwabuchi N., et al., "Effect of *Bifidobacterium breve* B-3 on skin photoaging induced by chronic UV irradiation in mice," *Benef. Microbes* (2015) 6: 497-504; Ishii Y., Sugimoto S., Izawa N., et al., "Oral administration of *Bifidobacterium breve* attenuates UV-induced barrier perturbation and oxidative stress in hairless mice skin," *Arch. Dermatol. Res.* (2014) 306: 467-73). Studies with *Bifidobacterium breve* fermented milk in human volunteers showed that fermented milk intake improved skin hydration (Mori N., Kano M., Masuoka N., et al., "Effect of probiotic and prebiotic fermented milk on skin and intestinal conditions in healthy young female students," *Biosci. Microbiota Food Health* (2016) 35:105-112).

However, it is not clear how the probiotics are mechanistically affecting the skin and how they may globally affect the skin's biomechanical properties, such as sebum production, transepidermal water loss, and skin hydration. Although there was a previous study looking at how fermented food shifted skin hydration (Mori, et al., 2016), there is not a study that has utilized a probiotic supplement to assess how sebum and the skin's barrier properties were affected.

Accordingly, there exists a need for probiotic compositions having a biological or therapeutic activity on the epidermis. If a new probiotic composition having a biological or therapeutic activity on the epidermis could be found, this would represent a useful contribution to the art.

SUMMARY OF THE INVENTION

In an embodiment, the present disclosure relates to a method of administration of a spore-based probiotic composition for modulating dermal and sub-dermal properties of a subject.

The method includes administering to a human subject an effective amount of a spore-based probiotic composition comprising strains *Bacillus indicus* (HU36), *Bacillus subtilis* (HU58), *Bacillus coagulans* SC-208, *Bacillus clausii* SC-109, and *Bacillus licheniformis*, each strain comprising *Bacillus* spores.

DETAILED DESCRIPTION

Figure 1:
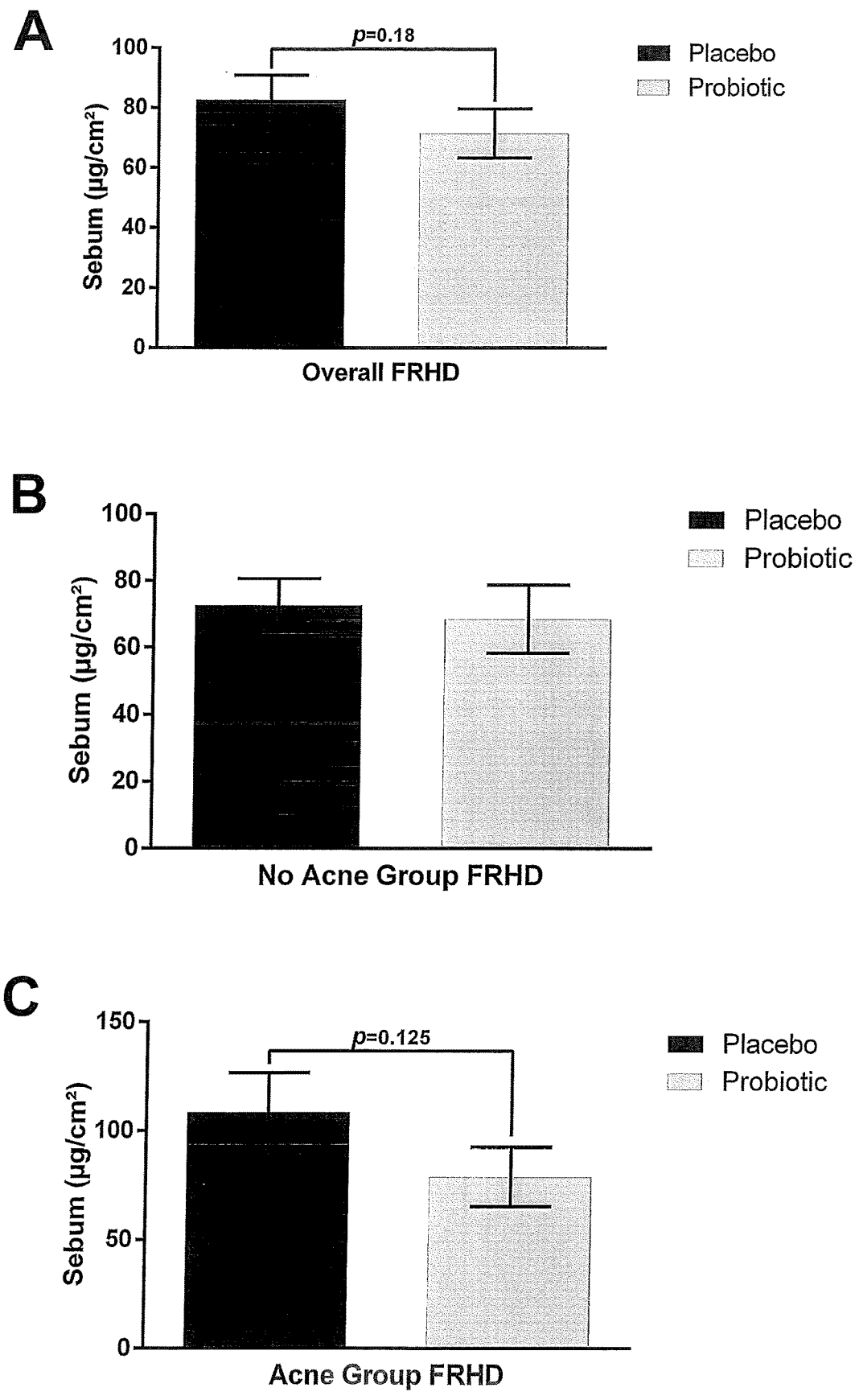
FIG. 1 depicts sebum excretion. Sebum measurements were made in the overall population and then subdivided into acne and no acne groups and were given placebo for four weeks followed by four weeks of probiotics. Sebum excretion was measured on the forehead at the end of each treatment. (A) Overall sebum production had a trend toward decreasing after probiotic treatment. (B) In the no acne group (n=18), the sebum production was unchanged in the placebo and the probiotic treatment groups. (C) In the group with acne (n=7) there was a trend (p=0.125) toward a decrease in the sebum excretion in the probiotic group. Error bars represent mean+SEM, *p=<0.05.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possible that more than one of the elements are present, unless the context clearly requires that there is one and only one of the elements. The indefinite article "a" or "an" thus usually means "at least one."

As used herein, an "effective amount" or an "amount effective for" is defined as an amount effective, at dosages and for periods of time necessary, to achieve a desired biological result, such as reducing, preventing, or treating a disease or condition and/or inducing a particular beneficial effect. The effective amount of compositions of the disclosure may vary according to factors such as age, sex, and weight of the individual. Dosage regime may be adjusted to provide the optimum response. Several divided doses may be administered daily, or the dose may be proportionally reduced as indicated by the exigencies of an individual's situation. As will be readily appreciated, a composition in accordance with the present disclosure may be administered in a single serving or in multiple servings spaced throughout the day. As will be understood by those skilled in the art, servings need not be limited to daily administration, and may be on an every second or third day or other convenient effective basis. The administration on a given day may be in a single serving or in multiple servings spaced throughout the day depending on the exigencies of the situation.

As used herein, the term "subject" or "individual" refers to any vertebrate including, without limitation, humans and other primates (e.g., chimpanzees and other apes and monkey species), farm animals (e.g., cattle, sheep, pigs, goats, and horses), domestic animals (e.g., dogs and cats), laboratory animals (e.g., rodents such as mice, rats, and guinea pigs), and birds (e.g., domestic, wild, and game birds such as chickens, turkeys, and other gallinaceous birds, ducks, geese, and the like). In some implementations, the subject may be a mammal. In other implementations, the subject may be a human.

In various embodiments, the present disclosure provides probiotic compositions, methods of producing these probiotic compositions, and methods of favorably modulating properties of dermal and sub-dermal layers of skin by administering an effective amount of the probiotic compositions to a subject in need thereof. In other embodiments of the present invention, the probiotic compositions of the present disclosure increase skin hydration, reduce wrinkly appearance, reduce sebum content, reduce skin inflammation, change the lipidome on the skin, change the skin microbiota, and/or reduce the appearance and frequency of acne lesions or rosacea. In yet other embodiments of the present invention, a composition of two or more probiotic strains of the present disclosure creates an unexpected synergy that favorably modulates properties of dermal and sub-dermal layers of skin. In yet other embodiments of the present invention, a composition of two or more probiotic strains of the present disclosure creates an unexpected synergy that increases skin hydration, reduces wrinkly appearance, reduces sebum content, reduces skin inflammation, changes the lipidome on the skin, changes the skin microbiota, and/or reduces the appearance and frequency of acne lesions or rosacea. These effects have been experimentally verified based on supplementation of study participants with a composition comprising one or more colonizing probiotic material strains that may be spore-based probiotic bacterial strains.

In embodiments of the present invention, the probiotic compositions may contain a probiotic microorganism that in some applications may be a spore-based probiotic organism selected from the following genuses: *Lactobacillus, Bifidobacterium, Lactococcus, Propionibacterium, Bacillus, Enterococcus, Escherichia, Streptococcus, Pediococcus*, and *Saccharomyce*. In certain aspects, the probiotic microorganism is at least one of *Lactobacillus acidophilus, Lactobacillus rhamnosus, Lactobacillus fermentum, Lactobacillus casei, Lactobacillus bulgaricus, Lactobacillus gasseri, Lactobacillus helveticus, Lactobacillus johnsonii, Lactobacillus lactis, Lactobacillus plantarum, Lactobacillus reuteri, Lactobacillus salivarius, Lactobacillus paracasei, Bifidobacterium sp., Bifidobacterium longum, Bifidobacterium infantis, Bifidobacterium animalis, Bifidobacterium bifidum, Bifidobacterium adelocentis, Bifidobacterium lactis, Bacillus subtilis, Bacillus coagulans, Bacillus licheniformis, Enterococcus faecalis, Enterococcus faecium, Lactococcus lactis, Streptococcus salivarius, Saccharomyces cerevisiae*, and *Saccharomyces boulardii*. The probiotic microorganism may be in the form of spores or in a vegetative state.

The *Lactobacillus* genus is extremely diverse and expanding every year. With over 230 species, it has grown into one of the biggest genera in the bacterial taxonomy. As the genus has exceeded the acceptable "normal diversity," renaming and re-classification is inevitable wherein the genus *Lactobacillus* may be split into most likely twelve new genera. Many traditional "probiotic" species with substantiated industrial importance and starter cultures many no longer eventually be called "*Lactobacillus*." Hence, a substantial communication challenge looms ahead to reduce the inevitable confusion regarding the "old commercial" and "correct scientific" nomenclature. Once the International Committee on Systematics of Prokaryotes publishes new nomenclature in their official journal, the INTERNATIONAL JOURNAL OF SYSTEMATIC AND EVOLUTIONARY MICROBIOLOGY, the changes are valid and official. The manuscript that will be submitted for publication outlining the new nomenclature of the *Lactobacillus* genus will likely be ready for submission by the end of 2018. Meanwhile, there was a taxonomic subcommittee meeting in September 2018 to discuss the nomenclature changes and an (invite-only) expert LABIP workshop in October 2018 that will evaluate the science while considering the consequences for regulations, legal/IP, and industry.

Probiotics are measured by colony forming units ("CFUs"). Few studies have been done to determine effective dosages, but effective dosages are usually in the hundreds of millions of CFUs or higher. If probiotics are being used to help with digestion, probiotics should be taken with meals, but otherwise the probiotics may survive better if taken between meals, particularly if taken with liquids that help to dilute stomach acid and move the probiotics more quickly into the digestive tract. Probiotics may be given short-term or long-term.

In some implementations, the concentration of the probiotic microorganism in the composition may be at least about $1 \cdot 10^9$ CFU/g, at least about $2 \cdot 10^9$ CFU/g, at least about $3 \cdot 10^9$ CFU/g, at least about $4 \cdot 10^9$ CFU/g, at least about $5 \cdot 10^9$ CFU/g, at least about $6 \cdot 10^9$ CFU/g, at least about $7 \cdot 10^9$ CFU/g, at least about $8 \cdot 10^9$ CFU/g, at least about $9 \cdot 10^9$ CFU/g, at least about $1 \cdot 10^{10}$ CFU/g, at least about $2 \cdot 10^{10}$ CFU/g, at least about $3 \cdot 10^{10}$ CFU/g, at least about $4 \cdot 10^{10}$ CFU/g, at least about $5 \cdot 10^{10}$ CFU/g, at least about $6 \cdot 10^{10}$ CFU/g, at least about $7 \cdot 10^{10}$ CFU/g, at least about $8 \cdot 10^{10}$ CFU/g, at least about $9 \cdot 10^{10}$ CFU/g, or at least about $1 \cdot 10^{11}$ CFU/g.

The spore-based probiotic supplement may comprise spores having a survival rate within any of the following ranges after exposure to gastric acid in situ: about 75% to about 99%, about 80% to about 95%, about 85% to about 90%, and greater than about 90%.

The spore-based probiotic supplement may comprise a number of spores within any of the following ranges: about 1 billion to about 10 billion spores, about 1.5 billion spores to about 9.5 billion spores, about 2 billion spores to about 9 billion spores, about 2.5 billion spores to about 8 billion spores, about 3 billion spores to about 7 billion spores, about 3.5 billion spores to about 6.5 billion spores, about 3.5 billion spores to about 6 billion spores, about 3.5 billion spores to about 5 billion spores, and about 3.5 billion spores to about 4.5 billion spores.

The spore-based probiotic supplement may comprise a liquid, confectionary item, powder or pill form or may be added to a food product. In one implementation, about $1 \cdot 10^{10}$ CFU of microorganism is present in each gram of bulk, dried raw powder where each gram contains about 60% or less of bacterial mass and about 40% carrier system. In other implementations, each gram contains about 70% or less of bacterial mass and about 30% carrier system, about 80% or less of bacterial mass and about 20% carrier system, about 90% or less of bacterial mass and about 10% carrier system, about 50% or less of bacterial mass and about 50% carrier system, about 40% or less of bacterial mass and about 60% carrier system, about 30% or less of bacterial mass and about 70% carrier system, about 20% or less of bacterial mass and about 80% carrier system, or about 10% or less of bacterial mass and about 90% carrier system.

Implementations of the methods and compositions disclosed herein may comprise a spore-based probiotic. A spore-based probiotic is comprised of endosomes which are highly resistant to acidic pH, are stable at room temperature, and deliver a much greater quantity of high viability bacteria to the small intestine than traditional probiotic supplements. Traditional micro-encapsulation uses live microorganisms which are then micro-encapsulated in an effort to protect the microorganisms; however, this is a process that inherently leads to the eventual death of the microorganisms thereby reducing the efficacy of the microorganisms. Using spore-based microorganisms that have been naturally microencapsulated to form endosomes may be preferable as these microorganisms are dormant and do not experience a degradation in efficacy over time. These spore-based microorganisms are also particularly thermally stable and can survive UV pasteurization, so they are also able to be added to food products or beverages prior to thermal exposure or UV pasteurization without experiencing a degradation in efficacy over time.

Probiotic supplementation may be beneficial in skin disease such as atopic dermatitis and acne. Probiotics regulate the gut microbiome, along with having anti-inflammatory effects locally in the gut and systemically away from the gut.

This study described herein adds evidence supporting the use of probiotics in the treatment of dermatologic conditions to a growing movement in the scientific community trying to better understand the reach of the gut's microbiome.

This study also adds evidence for the use of spore based probiotics for shifting gut microbiota and the blood short chain fatty acids as well as its potential for use with acne.

Antibiotic therapy is widely used to treat various dermatological conditions. However, such widespread use can lead to antibiotic resistance which can affect the gut microbiome. Probiotic supplementation can be an alternative approach in modulating the gut microbiome along with having beneficial effects, such as in treatment do of atopic dermatitis and acne.

Micro-Encapsulation

In certain implementations, the probiotic microorganisms are microencapsulated prior to addition to the probiotic compositions. Micro-encapsulation is a process in which tiny particles or droplets are surrounded by a coating to give small capsules of many useful properties. In a relatively simple form, a microcapsule is a small sphere with a uniform wall around it. The material inside the microcapsule is referred to as the core, internal phase, or fill, whereas the wall is sometimes called a shell, coating, or membrane. Most microcapsules have diameters between a few micrometers and a few millimeters.

The definition of "microencapsulation" has been expanded, and includes most foods. Every class of food ingredient has been encapsulated; flavors are the most common. The technique of microencapsulation depends on the physical and chemical properties of the material to be encapsulated. See, e.g., L. S. Jackson & K. Lee, *Microencapsulation and the food industry*, LEBENSMITTEL-WISSENSCHAFT TECHNOLOGIE (Jan. 1, 1991), incorporated by reference herein in its entirety.

Many microcapsules, however, bear little resemblance to these simple spheres. The core may be a crystal, a jagged absorbent particle, an emulsion, a Pickering emulsion, a suspension of solids, or a suspension of smaller microcapsules. The microcapsule even may have multiple walls.

Various techniques may be used to produce microcapsules, and each of such various techniques will be understood by a person of ordinary skill in the art. These techniques that may be used to produce microcapsules include, but are not limited to, pan coating, air-suspension coating, centrifugal extrusion, vibrational nozzle, spray-drying, ionotropic gelation, interfacial polycondensation, interfacial cross-linking, in situ polymerization, and matrix polymerization, as described below.

Pan Coating

The pan coating process, widely used in the pharmaceutical industry, is among the oldest industrial procedures for forming small, coated particles or tablets. The particles are tumbled in a pan or other device while the coating material is applied slowly.

Air-Suspension Coating

Air-suspension coating, first described by Professor Dale Eavin Wurster at the University of Wisconsin in 1959, gives improved control and flexibility compared to pan coating. In this process, the particulate core material, which is solid, is dispersed into the supporting air stream and these suspended particles are coated with polymers in a volatile solvent leaving a very thin layer of polymer on them. This process is repeated several hundred times until the required parameters such as coating thickness, etc., are achieved. The air stream which supports the particles also helps to dry them, and the rate of drying is directly proportional to the temperature of the air stream which can be modified to further affect the properties of the coating.

The re-circulation of the particles in the coating zone portion is effected by the design of the chamber and its operating parameters. The coating chamber is arranged such that the particles pass upwards through the coating zone, then disperse into slower moving air and sink back to the base of the coating chamber, making repeated passes through the coating zone until the desired thickness of coating is achieved.

Centrifugal Extrusion

Liquids are encapsulated using a rotating extrusion head containing concentric nozzles. In this process, a jet of core liquid is surrounded by a sheath of wall solution or melt. As the jet moves through the air it breaks, owing to Rayleigh instability, into droplets of core, each coated with the wall solution. While the droplets are in flight, a molten wall may be hardened or a solvent may be evaporated from the wall solution. Because most of the droplets are within +10% of the mean diameter, they land in a narrow ring around the spray nozzle. Hence, if needed, the capsules can be hardened after formation by catching them in a ring-shaped hardening bath. This process is excellent for forming particles 400-2,000 μm in diameter. Because the drops are formed by the breakup of a liquid jet, the process is only suitable for liquid or slurry. A high production rate can be achieved, i.e., up to 22.5 kg (50 lb) of microcapsules can be produced per nozzle per hour per head. Heads containing 16 nozzles are available.

Vibrational Nozzle

Core-Shell encapsulation or Microgranulation (matrix-encapsulation) can be done using a laminar flow through a nozzle and an additional vibration of the nozzle or the liquid. The vibration has to be done in resonance of the Rayleigh instability and leads to very uniform droplets. The liquid can consist of any liquids with limited viscosities (0-10,000 mPa·s have been shown to work), e.g., solutions, emulsions, suspensions, melts, etc. The solidification can be done according to the used gelation system with an internal gelation (e.g., sol-gel processing, melt) or an external (additional binder system, e.g., in a slurry). The process works very well for generating droplets between 20-10,000 μm, applications for smaller and larger droplets are known. The units are deployed in industries and research mostly with capacities of 1-20,000 kg per hour (2-44,000 lb/h) at working temperatures of 20-1500° C. (68-2732° F.) (room temperature up to molten silicon). Nozzle heads with from one up to several hundred thousand nozzles are available.

Spray-Drying

Spray drying serves as a microencapsulation technique when an active material is dissolved or suspended in a melt or polymer solution and becomes trapped in the dried particle. The main advantages are the abilities to handle labile materials because of the short contact time in the dryer; in addition, the operation is economical. In modern spray dryers the viscosity of the solutions to be sprayed can be as high as 300 mPa·s. By combining this technique with the use of supercritical Carbon Dioxide, sensitive materials like proteins can be encapsulated.

Ionotropic Gelation

The coacervation-phase separation process consists of three steps carried out under continuous agitation:
(1) Formation of 3 immiscible chemical phases: liquid manufacturing vehicle phase, core material phase, and coating material phase.
(2) Deposition of coating: core material is dispersed in the coating polymer solution. Coating polymer material coated around core. Deposition of liquid polymer coating around core by polymer adsorbed at the interface formed between core material and vehicle phase.
(3) Rigidization of coating: coating material is immiscible in vehicle phase and it gets rigid in form. Techniques for rigidization include thermal, cross-linking, or dissolvation.

Interfacial Polycondensation

In interfacial polycondensation, the two reactants in a polycondensation meet at an interface and react rapidly. The basis of this method is the classical Schotten-Baumann reaction between an acid chloride and a compound containing an active hydrogen atom, such as an amine or alcohol, a polyester, a polyuria, or a polyurethane. Under the right conditions, thin flexible walls form rapidly at the interface. A solution of the pesticide and a diacid chloride are emulsified in water and an aqueous solution containing an amine and a polyfunctional isocyanate is added. Base is present to neutralize the acid formed during the reaction. Condensed polymer walls form instantaneously at the interface of the emulsion droplets.

Interfacial Cross-Linking

Interfacial cross-linking is derived from interfacial polycondensation, and was developed to avoid the use of toxic diamines, for pharmaceutical or cosmetic applications. In this method, the small bifunctional monomer containing active hydrogen atoms is replaced by a biosourced polymer, like a protein. When the reaction is performed at the interface of an emulsion, the acid chloride reacts with the various functional groups of the protein, leading to the formation of a membrane. The method is very versatile, and the properties of the microcapsules (size, porosity, degradability, mechanical resistance) may be varied. Flow of artificial microcapsules in microfluoridic channels is contemplated.

In-Situ Polymerization

In a few microencapsulation processes, the direct polymerization of a single monomer is carried out on the particle surface. In one process, e.g., cellulose fibers are encapsulated in polyethylene while immersed in dry toluene. Usual deposition rates are about 0.5 μm/min. Coating thickness ranges 0.2-75 μm (0.0079-3.0 mils). The coating is uniform, even over sharp projections. Protein microcapsules are biocompatible and biodegradable, and the presence of the protein backbone renders the membrane more resistant and elastic than those obtained by interfacial polycondensation.

Matrix Polymerization

In a number of processes, a core material is imbedded in a polymeric matrix during formation of the particles. A simple method of this type is spray-drying, in which the particle is formed by evaporation of the solvent from the matrix material. However, the solidification of the matrix also can be caused by a chemical change.

This invention is further illustrated by the following additional examples that should be construed as limiting. Those of skill in the art should, in light of the present disclosure, appreciate that many changes can be made to the specific embodiments that are disclosed and still obtain a like or similar result without departing from the spirit and scope of the invention.

EXAMPLES

Example 1: The Influence of Oral Probiotics on the Microbiome and Lipidome

A. Objectives

The purpose of this study is to assess how oral probiotics can alter the microbiome of the gut and skin, and the lipidome of the gut, blood, and skin. The primary objective is to assess if probiotics rich in the production of short chain fatty acids ("SCFAs") can shift the blood lipidome to have a higher level of SCFAs.

B. Background

Antibiotics are widely used within dermatology for the treatment of chronic skin conditions such as acne, rosacea, and atopic dermatitis. Previous studies have shown that oral probiotics may be beneficial for skin diseases such as atopic dermatitis and acne, but a mechanism by which the gut communicates to the skin remains elusive. See, e.g., M. K. Trivedi, et al., *Emerging Therapies for Acne Vulgaris*, 19 AM. J. CLINICAL DERMATOLOGY 505 (2018); M. Notay, et al., *Probiotics, Prebiotics, and Synbiotics for the Treatment and Prevention of Adult Dermatological Diseases*, 18 AM. J. CLINICAL DERMATOLOGY 721 (2017); each of which is incorporated by reference herein in its entirety.

The balance between SCFAs and long chain fatty acids ("LCFAs") has been proposed as one factor in how bacteria in the gut are able to communicate with the rest of the body. Studies have shown that subjects with acne have a reduced level of SCFAs in their blood when compared to age-matched control.

The aim of this study is to understand how oral probiotics may alter the gut microbiome and if they can augment the SCFAs in the blood lipidome. Ultimately, the goal is to find suitable alternatives for the use of antibiotics in the treatment of chronic skin conditions so that the amount of antibiotics in use can be reduced.

C. Inclusion and Exclusion Criteria

Inclusion Criteria:

18 years of age or older.

Exclusion Criteria:

Those on oral antibiotics within a month of initiating the study;

Subjects must have no history of diabetes, known cardiovascular disease, malignancy, kidney disease, or chronic steroid use;

Those with BMI higher than 30 $kg/m^2$;

Those on topical medications for the face, such as retinoids or antibiotics, who are not willing or who are medically unable (in the judgment of the investigator) to discontinue use for two weeks prior to the study and for the duration of study participation;

Those that have undergone a change in hormonally based therapies, including, but not limited to, oral contraceptive pills or progesterone-based pills within the last two months (progesterone-releasing IUDs are considered hormone-releasing therapy);

Those using medications that alter blood lipids, such as statins and anti-hyperlipidemic medications;

Current tobacco smokers, or those who have smoked tobacco over the past year, or a 5-year history of smoking tobacco;

Pregnant women;

Prisoners; and

Adults unable to consent.

D. Study Timelines

Each study participant will participate in the study for two months and the entire study will be conducted over the course of a year.

E. Study Endpoints

Primary Endpoint(s):

(1) Blood lipidome changes—specifically, the presence of SCFAs.

Secondary Endpoint(s):

(1) Gut microbiome changes—specifically, the presence of SCFA-producing bacteria;

(2) Sebum production, measured by sebumeter;

(3) Transepidermal water loss ("TEWL");

(4) Hydration;

(5) Skin microbiome changes;

(6) Gut lipidome changes; and (7) skin lipidome changes.

F. Procedures Involved

Twenty-five (25) subjects meeting the inclusion criteria, without any of the exclusion criteria, will be enrolled in this study. This study will be an open-label, single-blinded, placebo-controlled study, assessing the influence of probiotics. We have selected 25 subjects as a suitable sample for a pilot study, because a power analysis is not possible, as there are no previous studies evaluating changes in the blood lipidome.

First 4 weeks—placebo tablet daily:

Supplement appearing similar to probiotic formulations;

Each placebo tablet will contain rice flour only; and

Dose—2 tablets per day.

Second 4 weeks—probiotic tablet daily:

Probiotic formula (containing 5 strains): 4 billion ($4 \cdot 10^9$) CFUs, including HU36 (a strain of *Bacillus indicus*); HU58 (a strain of *Bacillus subtilis*); SC109 (a strain of *Bacillus clausii*); SC208 (a strain of *Bacillus coagulans*); and *Bacillus licheniformis*.

HU36 (Colorspore™) is a strain of *Bacillus indicus*, a preparation of which is manufactured by Viridis BioPharma Pvt. Ltd., Mumbai, India. The National Collection of Industrial, Food and Marine Bacteria ("NCIMB") Ltd. assigned strain number for *Bacillus indicus* HU36 is 41361.

HU58 ("ProBiotene™") is a strain of *Bacillus subtilis*, a preparation of which is manufactured by Viridis BioPharma Pvt. Ltd., Mumbai, India. *Bacillus subtilis* HU58 has been deposited with the National Center for Biotechnology Research under the accession number EF101709. The *Bacillus* Genetic Stock Center ("BGSC") assigned number for *Bacillus* HU58 is 3A34, and the NCIMB Ltd. assigned strain number is 30283.

SC109 is a strain of *Bacillus clausii*, a preparation of which was manufactured by Synergia Life Sciences Pvt. Ltd., Mumbai, India in March 2018. *Bacillus clausii* SC109 has been deposited with the Liebniz Institute DSMZ-German Collection of Microorganisms and Cell Cultures under the accession number DSM 32639.

SC208 is a strain of *Bacillus coagulans*, a preparation of which was manufactured by Synergia Life Sciences Pvt. Ltd., Mumbai, India in March 2018. *Bacillus coagulans* SC208 has been deposited with the Liebniz Institute DSMZ-German Collection of Microorganisms and Cell Cultures under the accession number DSM 32640.

Dose: 2 tablets per day, with a total daily dose of 4 billion ($4 \cdot 10^9$) CFUs.

Placebo and probiotic tablets will be supplied from Microbiome Labs.

G. Procedures Related to Research

Urine Pregnancy Test (for female subjects that have not had a hysterectomy) (see Table 1 for timeline):

There are no known risks to pregnant women, but pregnant women will not be enrolled in the study. Women will be counseled on the need to avoid pregnancy and the use of acceptable birth control that includes the following:

1. Abstinence; or

2. Two forms from the following acceptable forms of birth control:

Male latex condom;

Female condom;

Oral contraceptive pill;

Depot-based progestin contraceptive; or

Intrauterine device.

Stool Collection

Stool samples will be collected from subjects. Subjects will be given an instruction sheet to complete collection. These samples will be de-identified. See Table 1 for timeline.

Venipuncture

Up to 5 milliliters of blood will be collected with the standard venipuncture technique and stored at −80° C. prior to analysis. The blood will be used to establish baseline values to compare to endpoint values. We will be collecting blood to assess baseline and endpoint values of SCFAs, LCFAs, lipid mediator profiles, antioxidant status, and inflammatory cytokines, to correlate with the microbiome assessments. The subjects will be asked to fast for six hours prior to the blood draw before their study visits. See Table 1 for timeline.

Skin Microbiome

Cotton swabs will be performed on the face. See Table 1 for timeline.

Skin Microcomedome

An adhesive pore-cleansing strip, such as a Bioré strip, will then be applied to the face, and gently removed. See Table 1 for timeline.

Sebutape Collection

Sebutape (CuDerm, Dallas, Tex.) is a painless, non-invasive, adhesive patch that is placed on the skin to allow for absorption of secreted sebum. The adhesive patches can then be subsequently removed to allow for analysis of the collected sebum. Prior to Sebutape application, the applicant's face is cleaned with 70% isopropyl alcohol wipes. Sebutapes will be placed on the face of the subject. Sebutapes will be applied for up to one hour using disposable gloves and forceps. On removal, the Sebutape patches will be stored on sebutape Clear View PRO storage cards at −80° C. prior to analysis. The freezer is located in a locked and secure room. See Table 1 for timeline.

Sebumeter

Sebumeter measures will be performed (See Table 1 for timeline). The sebumeter device carries minimal risk because it is a non-invasive, painless device that requires only touching the skin for 30 seconds. The sebumeter device allows for the non-invasive and painless measurement of sebum secretion and has been used in multiple, IRB-approved studies.

Transepidermal Water Loss ("TEWL") and Collection

TEWL measurements will be performed (See Table 1 for timeline). This is a non-invasive, painless device that allows for a measurement of the barrier function of the stratum corneum. This non-invasive device has been widely used for the study of skin barrier function. Each device has a flat-top electrode that will come in contact with the skin surface during measurements. Each collection will take less than 1 minute. The subjects will not experience discomfort during and after the measurements.

Hydration Collection

Hydration measurements will be performed (See Table 1 for timeline). This is a non-invasive, painless device that allows for a measurement of the barrier function of the stratum corneum. This non-invasive and painless device has been widely used for the study of skin barrier function. Each device has a flat-top electrode that will come in contact with the skin surface during measurements. Each collection will take less than 1 minute. The subjects will not experience discomfort during and after the measurements.

Facial Photographs

Facial photographs using a digital camera will be obtained for all subjects. There will be no ultraviolet exposure. See Table 1 for timeline.

Food Record

Food diaries/logs will be given to track diet for specified days.

Digestion Questionnaire

A digestion questionnaire will be given to better understand and track digestive health in subjects.

H. All Subjects

Screening/Consent (Visit 1):
(1) Consent process;
(2) Medical and surgical history will be noted;
(3) Study team will review any medications and supplements subject is consuming;
(4) Instructions on how to complete food diaries/logs will be given;
(5) Stool kit will be given;
(6) Potential for washout prior to baseline and after screening if the patient has been used topical medications, antibiotics, and probiotics.

Baseline Visit (Visit 2) (Minimum 3 Days after Screening Visit):
(1) Urine pregnancy test (for applicable female subjects);
(2) Facial swabs;
(3) Sebutape collection from the face;
(4) Stool sample to be collected;
(5) Second stool sample kit will be given;
(6) Adhesive pore strip;
(7) Venipuncture blood collection;
(8) Facial photography;
(9) Sebumeter measurement;
(10) TEWL measurement;
(11) Hydration measurement;
(12) Previous food diary/log will be collected;
(13) New food diary/log will be given;
(14) Digestion questionnaire will be given and collected;
(15) Intervention/pill log will be given;
(16) Interventional supplement will be disbursed.

Week 4 Visit (+/−1 Week) (Visit 3):
(1) Urine pregnancy test (for applicable female subjects);
(2) Facial swabs;
(3) Sebutape collection from the face;
(4) Stool sample to be collected;
(5) Stool sample kit will be given;
(6) Adhesive pore strip;
(7) Venipuncture blood collection;
(8) Facial photography;
(9) Sebumeter measurement;
(10) TEWL measurement;
(11) Hydration measurement;
(12) Previous food diary/log will be collected;
(13) New food diary/log will be given;
(14) Digestion questionnaire will be given and collected;
(15) Previous study agent log will be collected;
(16) Intervention/pill log will be given;
(17) Interventional supplement will be disbursed;
(18) Pills collected and counted from previous month's supply.

Week 8 Visit (+/−Week) (Visit 4):
(1) Urine pregnancy test (for applicable female subjects);
(2) Facial swabs;
(3) Sebutape collection from the face;
(4) Stool sample to be collected;
(5) Adhesive pore strip;
(6) Venipuncture blood collection;
(7) Facial photographs;
(8) Sebumeter measurement;
(9) TEWL measurement;
(10) Hydration measurement;
(11) Adverse effects noted;
(12) Food diary/log will be collected;
(13) Digestion questionnaire will be given and collected;
(14) Intervention/pill log will be collected;
(15) Pills collected and counted from previous month's supply.

All collected samples (blood, adhesive strips, stool, and Sebutape) will be de-identified and coded. Only the research team will have access to the key that matches the samples to the subjects. The key will be password protected and located in a locked room.

The table of procedures is as follows:

TABLE 1

Table of Procedures

| Study Procedure | Visit 1- Screening Visit | Visit 2- Baseline | Visit 3-4 Weeks (+/− 1 week) | Visit 4-8 Weeks (+/− 1 week) |
| --- | --- | --- | --- | --- |
| Screening and Consent | X | | | |
| Medical and Surgical Hx | X | | | |
| Review concomitant medication | X | | | |
| Initiate medical washout as needed | X | | | |
| Start topical skin cleanser | X | X | X | |
| Stop topical skin cleanser | | | | X |
| Start placebo | | X | | |
| Stop placebo | | | X | |
| Start probiotic | | | X | |
| Stop probiotic | | | | X |
| Stool collection | | X | X | X |
| Venipuncture (max of 5 mL) | | X | X | X |
| Skin swab for microbiome | | X | X | X |
| Bioré strip collection from face | | X | X | X |
| Sebutapes Measurements | | X | X | X |
| Sebumeter Measurements | | X | X | X |
| TEWL Measurements | | X | X | X |
| Hydration Measurement | | X | X | X |

TABLE 1-continued

Table of Procedures

| Study Procedure | Visit 1- Screening Visit | Visit 2- Baseline | Visit 3-4 Weeks (+/− 1 week) | Visit 4-8 Weeks (+/− 1 week) |
|---|---|---|---|---|
| Facial Photography | | X | X | X |
| Pregnancy Test | | X | X | X |
| Food records | | X | X | X |
| Digestion Questionnaire | | X | X | X |
| Pill Count | | | X | X |

I. Clinical Trial Early Findings (as shown in Table 2):

(1) The probiotic statistically significantly reduces sebum excretion rate compared to placebo;

(2) The probiotic statistically significantly increases skin hydration compared to placebo.

The clinical trial early findings are as follows:

TABLE 2

Clinical Trial Early Findings

| | Wrinkles | | Pigment Intensity | |
|---|---|---|---|---|
| | Placebo | Probiotic | Placebo | Probiotic |
| Mean | −0.421492228 | −5.894612876 | 1.019766353 | −2.173266866 |
| Stdev | 10.11716447 | 13.18505591 | 2.382050609 | 11.25631057 |
| Stderror | 2.207746286 | 2.877215084 | 0.519806058 | 2.456328345 |
| t-test | | 0.069560587 | | 0.105402146 |

Example 2: Placebo-Controlled, Rater Double-Blinded Assessment of Probiotic Supplementation on Sebum Production, Skin Barrier Function and Acne The objective was to prospectively assess how oral probiotics alter the skin's biophysical properties and sebum production. In addition, the study also sought to assess for changes in the gut microbiome and blood lipidome in order to correlate it to changes in the gut.

Methods and Results Summary

This was a double-blinded, 8-week study in which 25 participants were assigned to take placebo pills for the first four weeks, and probiotics for the other four weeks. Blood and gut collection, facial photograph, sebum production, transepidermal water loss (TEWL), and hydration measurements were done at baseline, 4-weeks and 8-weeks. A board-certified dermatologist blinded to study interventions, graded the inflammatory and non-inflammatory lesions in subjects with acne.

As described below, the skin's biophysical properties shifted after the probiotic supplementation with a tendency to decrease sebum excretion and increased TEWL overall. Subgroup analysis of those with acne showed improvement in total, non-inflammatory, and inflammatory lesion counts. Both LPS and FABP-2, markers of gut permeability, had improving trends after probiotic supplementation in the acne subgroup. The non-acne population had a shift in the gut microbiota with an increase relative abundance of *Akkermansia* while the acne population had an increase in the relative abundance of Lachnospiraceae and [*Ruminococcus*] *gnavus*. Overall, there was an augmentation of the acetate: propionate ratio on circulating short chain fatty acids.

The purpose of this study was to prospectively assess how oral probiotics can alter the skin biomechanical properties and sebum production. Included was a recruitment of participants with non-cystic acne to further stratify the population. Finally, changes were assessed in the gut microbiome and blood lipidome to correlate measurable changes in the skin to these factors.

Study Design

This study was conducted from June, 2018 to October, 2018 as a single-blinded, placebo controlled, 8-week study. This study was approved by the Institutional Review Board at the University of California, Davis and registered on ClinicalTrials.gov (NCT03605108). All participants provided written informed consent prior to participation and received financial compensation. Twenty-five healthy participants (mean age 30.8 years; range: 19-62 years) were recruited and screened for eligibility at the UC Davis Dermatology clinic. Participants were enrolled and assigned interventions by clinical research coordinator. Exclusion criteria included any topical antibiotic use for the past one month, a history of acute or chronic disease that would likely interfere with or increase the risk of study participation, individuals with BMI higher than 30 kg/m$^2$, subjects that started a new hormonal birth control agent or switched to a different hormonal birth control within the previous two month, individuals who were using or had used a retinoid during the previous 14 days, subjects who were using medications that alter blood lipids, such as statins and anti-hyperlipidemic medications. Participants with cystic acne were excluded but subjects with non-cystic acne were allowed as this is not considered a disease. Finally, subjects were excluded if they were current smokers, or those that have smoked tobacco over the past year, or a 5 year-pack year history of smoking tobacco.

The study was conducted over 8 weeks and consisted of five visits (consent, baseline, week 4 and week 8 follow up). Twenty-five subjects received placebo pills for the first four weeks, and the same twenty-five subjects received the probiotic formulation as in Example 1 (Megasporebiotic, Microbiome Labs, Saint Augustine, Fla.) which was a spore-based probiotic that included 4 billion spores from gram-positive, spore-forming strains [*Bacillus indicus* (HU36), *Bacillus subtilis* (HU58), *Bacillus coagulans, Bacillus licheniformis*, and *Bacillus clausii*] for the other four weeks. Subjects were instructed to take two tablets per day. Subjects were instructed to not wash their faces or body or apply any products to their faces on the day of their study visit.

Blood Collection

Fasted blood samples were collected at baseline, 4-weeks and 8-weeks to assess baseline and endpoint values of short chain fatty acids, long chain fatty acids, lipid mediator profiles, antioxidant status, and inflammatory cytokines to correlate this with the microbiome assessments.

Gut Microbiome Collection

Fecal stool samples were collected to determine how the gut microbiome and lipidome shifts at baseline, 4-weeks and 8-weeks. Subject were directed to place the stool collections immediately into the freezer after collection prior to their visits and all samples were placed in a −80° C. freezer immediately until they were utilized for analysis.

Facial Photography

High resolution photographs were obtained from all participants at baseline, week-4, and week-8 through the use of the BTBP 3D Clarity Pro® Facial Modeling and Analysis System (Brigh-Tex BioPhotonics, San Jose, Calif.). The photographic instrumentation takes automated photographs in zero extraneously ambient lighting with reproducible placement of the face and identical photographic exposures. This system has been validated in comparison to clinical grading of multiple facial features (Petukhova T. A., Foolad N., Prakash N., et al., "Objective volumetric grading of postacne scarring," *J. Am. Acad. Dermatol.* (2016) 75: 229-31; Foolad N., Prakash N., Shi V. Y., et al., "The use of facial modeling and analysis to objectively quantify facial redness," *J. Cosmet. Dermatol.* (2016) 15: 43-8; Ornelas J., Rosamilia L., Larsen L., et al., "Objective assessment of isotretinoin-associated cheilitis: Isotretinoin Cheilitis Grading Scale," *J. Dermatolog. Treat.* (2016) 27: 153-5; Foolad N., Shi V. Y., Prakash N., et al., "The association of the sebum excretion rate with melasma, erythematotelangiectatic rosacea, and rhytides," *Dermatol. Online J.* (2015) 21(6): 2; each incorporated by reference herein).

Facial Grading and Analysis

Facial photographs were evaluated by a board-certified dermatologist in a blinded fashion such that the rater and the participants were double-blinded to the interventions. Subjects with acne were assessed for changes in the acne by quantifying the inflammatory and non-inflammatory lesions. The sum of both inflammatory and non-inflammatory lesions were quantified as total lesion count.

Skin Barrier Function

The investigators assessed skin barrier function by measuring sebum production (Sebumeter® SM 815; Courage and Khazaka, Cologne, Germany), transepidermal water loss ("TEWL", using Vapometer; Delfin Technologies, Stamford, Conn.), and Hydration (MoistureMeterSC; Delfin Technologies, Stamford, Conn.) at baseline, 4-weeks and 8-weeks.

Statistical Analysis

The study participants were analyzed as an overall group and then subdivided into two groups, Acne and No Acne. The data was analyzed at baseline, 4-weeks and 8-weeks. The alpha was set to 0.05 and a repeated measure Wilcoxon test was used to perform statistical analysis. P-values were considered significant if they were less than 0.05, whereas they were reported as approaching significance if between 0.05 and 0.2.

Outcomes Measured

The primary outcome measures were to assess if probiotics could reduce sebum production after 4 weeks of probiotic supplementation. Secondary outcome measures included shifts in the gut microbiome, changes in the skin barrier biophysical properties, skin microbiome changes, and changes in the blood lipidome changes.

Microbiome Collection

Nasolabial and glabellar skin were swabbed under sterile conditions with sterile swabs to collect specimens for microbiome analysis at baseline, week-4, and week-8. Copan-e swabs (480C) were used to collect microbiome samples. Swabs were collected into 300 μL Copan-e buffer in sterile DNase free microfuge tubes in order to minimize sample volume. Swabs were stored at −80° C. until DNA was extracted. At each visit a non-invasive adhesive pore cleansing strip (Biore, Cincinnati, Ohio) was applied along with sebutapes (Cuderm, Dallas, Texas).

Fecal Sampling

Subjects were given at-home stool collection kits. Kits were expected to be done within 24 hours of the weeks 0, 4, and 8 visits. The subjects were instructed to keep the stool in their at-home freezer until they were to come to their visit. Stool collection kits included ice packs to keep the sample cool upon transport. Once collected by study team, the stool samples were kept in a 80° C. freezer until processing.

Microbiome Analysis

Fecal samples were defrosted on ice, then sterile spatulas were used to transfer 0.25±0.05 g fecal material into Qiagen PowerSoil (12888-100) bead tubes. After bead beating, samples were heat killed at 80° C. for 3 min, frozen, then thawed and treated with 10 mg/mL lysozyme for 2 h at 42° C. (C1 was added after this). DNA was eluted in 60 μL instead of 100 μL. Skin swabs were processed the same, except that the heat killing and lysozyme steps were performed prior to bead-beating.

The V3V4 region of the 16S rRNA gene was amplified for sequencing. The V3 F primer was the same for both fecal and skin samples:

5'-TCGTCGGCAGCGTCAGATGTGTATAAGAGACAG.

For the fecal samples, previously published V4 R primers were used (Walters W., Hyde E. R., Berg-Lyons D., et al., "Improved Bacterial 16S rRNA Gene (V4 and V4-5) and Fungal Internal Transcribed Spacer Marker Gene Primers for Microbial Community Surveys," *mSystems* (2016) 1(1) 1-10; incorporated by reference herein). V4 F skin microbiome specific primer was:

5'-GTCTCGTGGGCTCGGAGATGTGTATAAGAGACAG.

Phusion High-Fidelity DNA Polymerase (ThermoFisher F530L) was used for library preparation: 1 U polymerase, 2 mM MgCl2, 5% DMSO, 0.5 pM each primer, 0.2 mM dNTPs in a final reaction volume of 25 μL. 3 μL fecal DNA or 5 μL swab DNA was used per reaction. For reactions that did not result in bands, PCR was retried with more DNA (5 μL for fecal and 10 μL for swab).

The PCR program included a 2 min hot-start (98° C.), followed by 30 cycles of 98° C. for 30 s, 62° C. for 30 s, and 72° C. for 15 s, with a final extension at 72° C. for 30 s before pausing at 4° C. All samples were run on a gel to ensure the PCR was successful and quantified using the Qubit Fluorometer system. Samples were sent to the University of California Berkeley for barcoding and sequencing. 300 cycle paired-end sequencing was performed on the Illumina MiSeq platform.

Sequencing data was processed in Qiime2 (Caporaso J. G., Kuczynski J., Stombaugh J., et al., "QIIME allows analysis of high-throughput community sequencing data," *Nat. Methods* (2010) 7: 335-6, incorporated by reference herein). A variety of PCoA plots were constructed, Shannon diversity was calculated and compared by group and treatment, and t-tests, fold-changes, and Δ relative abundances were calculated for each taxon and compared across groups/treatments. Trends were visualized and variances were calculated per taxon as well. For abundant OTUs that were not well-resolved using the Qiime2 classifier, phylogenies were constructed to better place them and to parse or clump OTUs further. Type sequences were pulled from the Ribosomal Database Project (RDP) website; MEGA7 was used to align sequences and construct phylogenies (Cole J. R., Wang Q., Cardenas E. et al., "The Ribosomal Database Project: improved alignments and new tools for rRNA analysis," *Nucleic Acids Res.* (2009) 37: D141-5; Kumar S., Stecher G., Tamura K., "MEGA7: Molecular Evolutionary Genetics Analysis Version 7.0 for Bigger Datasets," *Mol. Biol. Evol.* (2016) 33: 1870-4; each incorporated by reference herein).

Short Chain Fatty Acid (SCFA) Quantification

Plasma SCFAs were isolated and quantified as dimethyl-tert-butylsilane (DiMTBS) derivatives by GC-MS. Specifically, plasma samples (250 µL) isolated from EDTA containing sampling tubes and aqueous calibration solutions, and procedural LC-MS water blanks were enriched with 5 µL of 5.24 mM d3-acetate and 0.259 mM d5-propionate (CDN), acidified with 15 µL 6 N hydrochloric acid, and extracted with 1 mL of MTBE. Samples were centrifuged for 5 min at 10,000 rcf and 0.5 mL of the supernatant was dried with ~100 mg of sodium sulfate for 10 min. A 100 µL sub-aliquot was incubated with 15 µL of MTBSTFA +1% TBDMS (Sigma-Aldrich, St. Louis, MO) at 50° C. for 90 min and allowed to sit at room temperature overnight. Samples were then enriched with 10 µL of 272 pM 15:1n5 methyl ester internal standard. Residues were separated on 6890 GC equipped with a 30 m×0.25 mm, 0.25 µm DB-5 ms and 5973N MSD (Agilent Technologies, Santa Clara, CA) using a 1:10 split of a 2 µL injection, electron impact ionization, and selected ion monitoring/full scan mass spectra generation. GC Parameters: Injection port—280° C.; Oven Program—100° C. (hold 2 min), 35° C./min to 280° C.; carrier gas—1.5 mL/min helium; Total flow—19 mL/min. Data were acquired and processed with MassHunter v B.08. Acetate was corrected for d3-acetate recoveries, while propionate and butyrate were corrected for d5-propionate recoveries.

Figure 10:
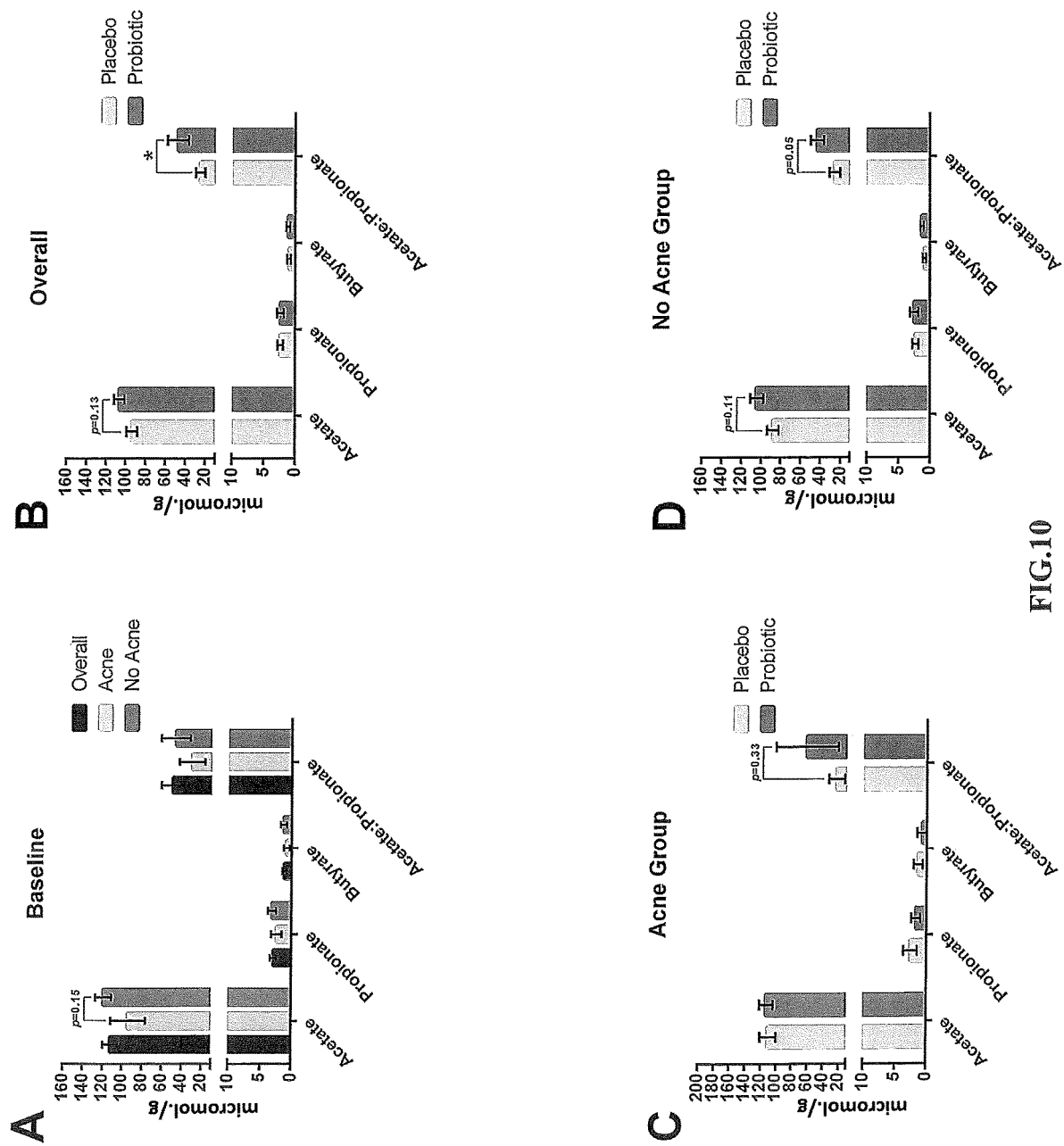
FIG. 10 depicts shift in blood short chain fatty acids. A) Short chain fatty acids were compared at baseline for the overall population (n=25), acne subpopulation (n=7), and the no acne subpopulation (n=18). There was a trend for a decrease in the acetate levels in those with acne (p=0.15). B) In the overall population probiotic supplementation led to an increasing trend in the acetate levels (p=0.13) and a significant increase in the acetate:propionate ratio. C) In the acne subpopulation there were no statistically significant changes with probiotic supplementation although was an 2.6-fold increase in the acetate:propionate ratio that was not statistically significant (p=0.33). D) Probiotic supplementation in the no acne group lead to an increasing trend in the acetate levels (p=0.11) and the acetate:propionate ratio (p=0.05). *p<=0.05.

Short chain fatty acid (SCFA) levels were tested and assessed in accordance with FIG. 10.

Study Results:

Skin Biophysical Properties

Changes in the skin's biophysical properties were followed to better assess changes in the skin barrier and the sebum production rate. Overall, the sebum excretion rate remained unchanged during the placebo intervention but there was a decrease after probiotic intervention that approached significance (FIG. 1, p=0.18). When the study participants were stratified by those with and without acne, the sebum excretion rate remained unchanged with placebo or probiotic exposure in the group without acne. However, the group with acne had a more marked decrease in the sebum excretion rate, but still only approached significance (FIG. 1, p=0.125) during the probiotic intervention although there was no change during the placebo intervention.

Figure 2:
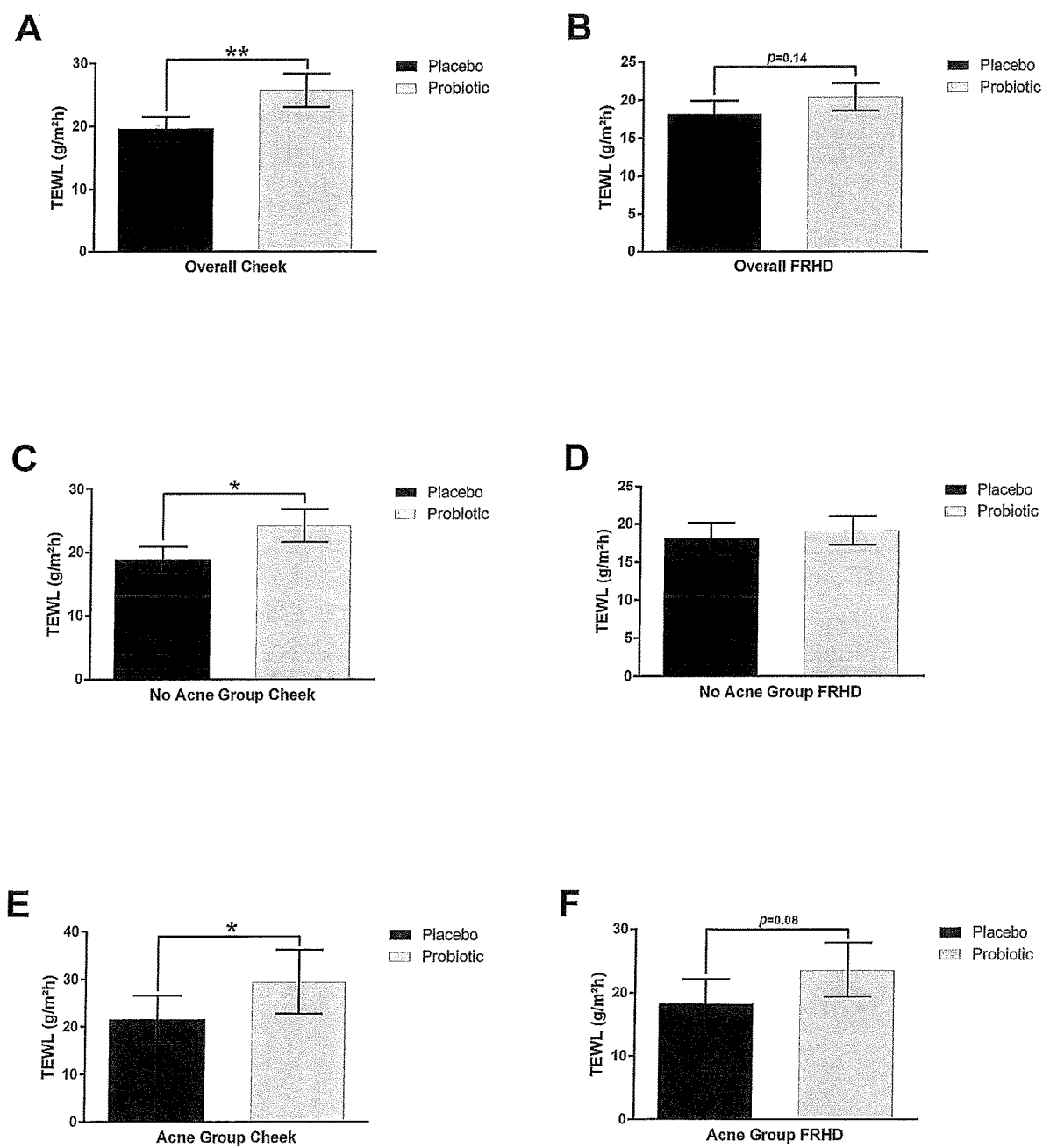
FIG. 2 depicts skin hydration. Skin hydration was measured on cheek and forehead after treating with four weeks of placebo followed by 4 weeks of probiotics. (A) Overall, skin hydration trended toward an increase (p=0.18) after probiotic supplementation on the cheeks. However, there was no difference noted on the forehead (B). Sub analysis of the no acne group on the cheeks (C) or forehead (D) did not reveal any significant differences. Subanalysis of the acne group did not reveal any differences on the cheek (E) or the forehead (F). Error bars represent mean+SEM, *p=<0.05.
Figure 3:
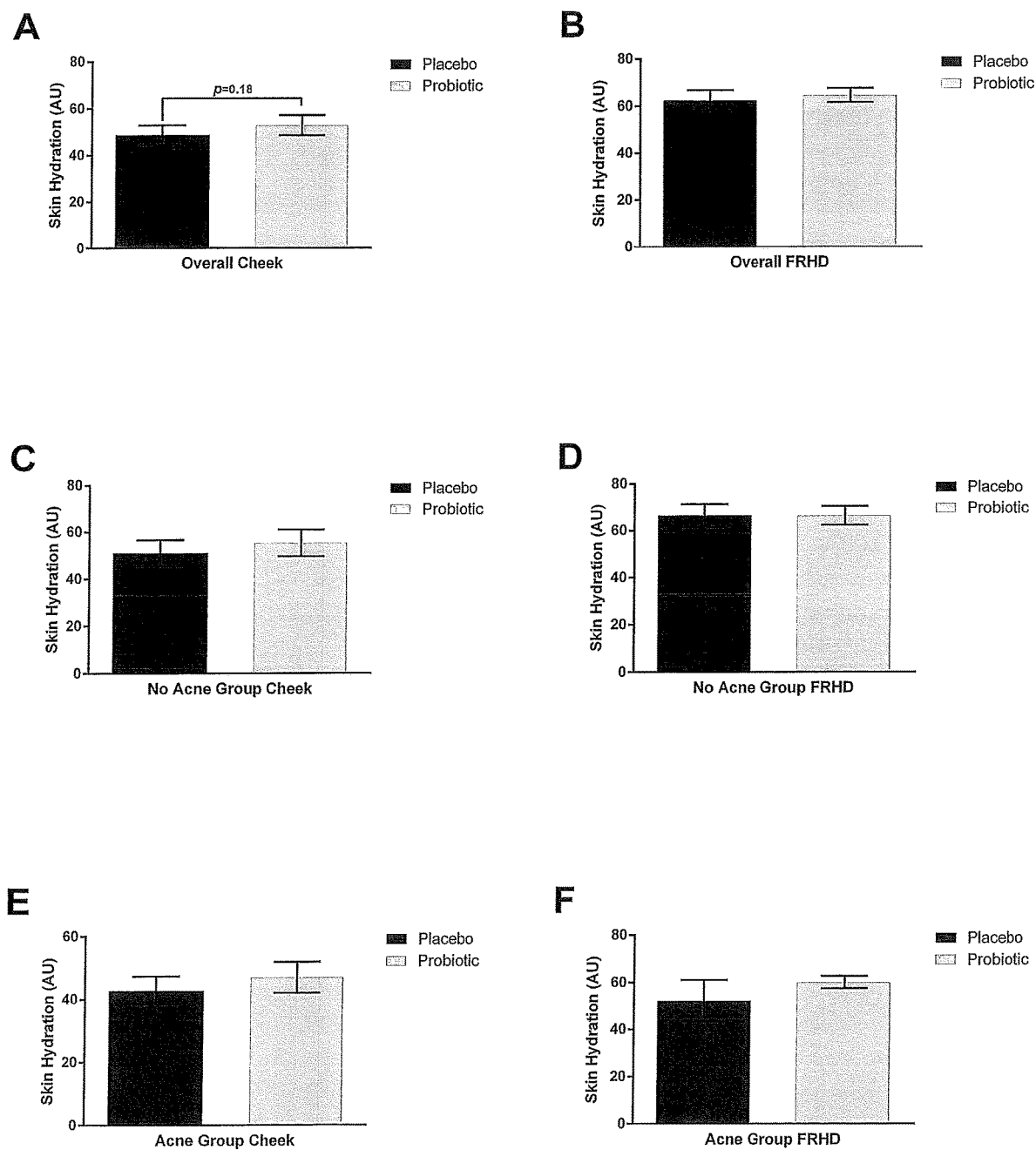
FIG. 3 depicts skin transepidermal water loss (TEWL). TEWL was measured after treating both groups with placebo and probiotics for four weeks. Overall TEWL on the cheek increased after probiotic treatment (A) and trended up on the forehead (B). In the no acne group, TEWL increased on the cheek (C) but not on the forehead (D). In the acne group, TEWL increased after probiotic treatment for both the cheek (E) and the forehead (F). Error bars represent Mean+SEM, *p=<0.05, **p=<0.01.

When measuring skin hydration, overall an increased hydration on the cheek in the probiotic group was observed to approach significance (FIG. 2, p=0.18), while no differences were found in forehead hydration or on any of the stratified populations. Transepidermal water loss (TEWL) on the cheeks was increased after probiotic exposure overall and after stratifying among those with and without acne (FIG. 3). The forehead TEWL was similarly increased in the overall population and the increase in the group with acne approached significance (p=0.08).

Gut Derived Proteins and TNF-Alpha

Figure 4:
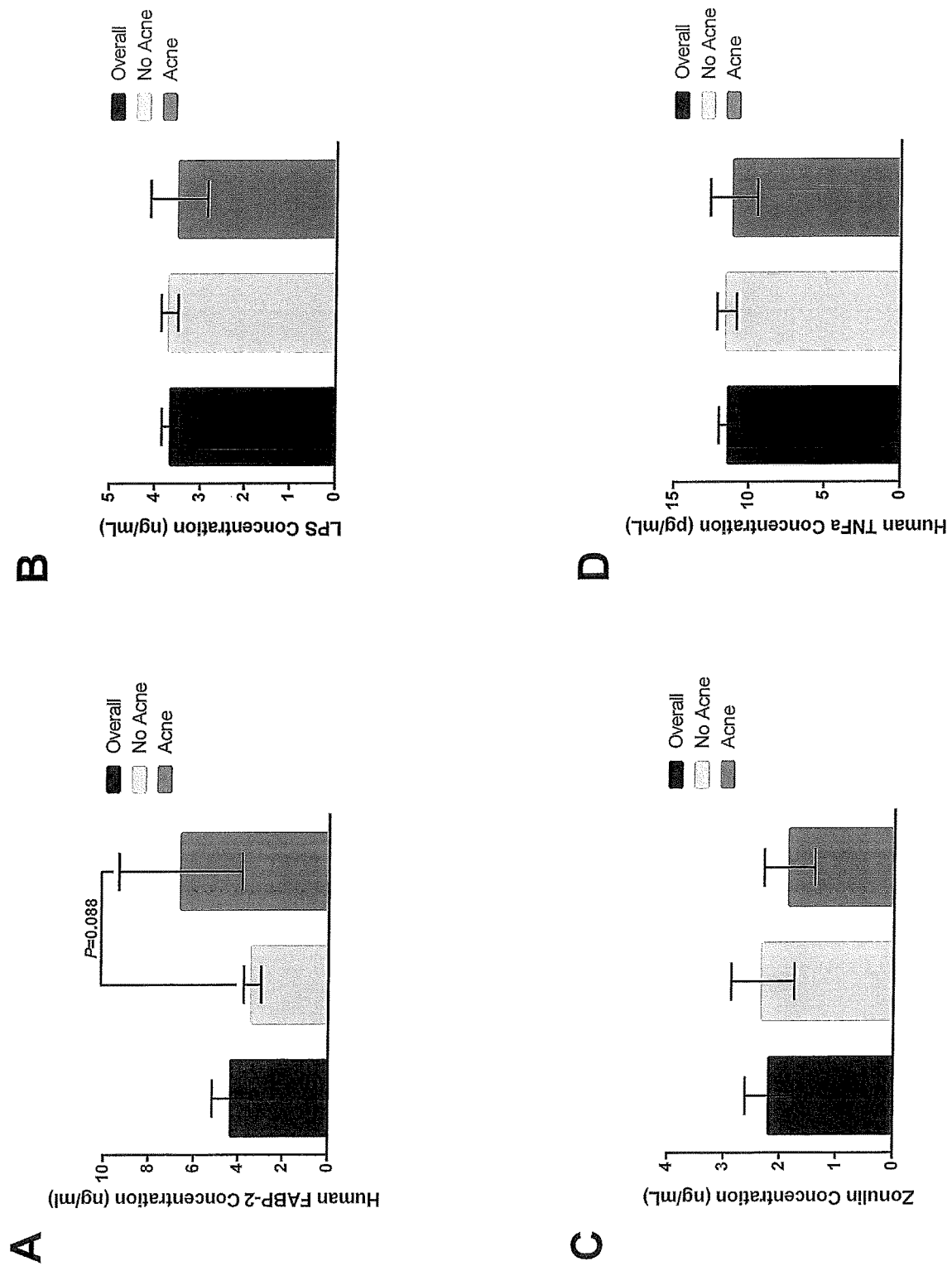
FIG. 4 depicts baseline markers of "leaky gut" and inflammation in the blood. Participants were divided into two groups based on the presence or absence of acne and their plasma concentration of enzymes were measured using ELISA at baseline. (A) Mean Human FABP-2 concentration trended up for acne in comparison to the no acne group (p=0.088). Neither Mean overall LPS (B), zonulin (C), nor the TNF-alpha (D) concentrations were different among the groups. Error bars represent Mean+SEM, *p=<0.05.

In order to understand how the placebo and probiotic interventions may be impacting inflammation and the concept of the "leaky gut" we evaluated the blood levels of several proteins at baseline and after interventional treatment. While gut derived markers were not elevated at baseline, the elevation in FABP-2 levels in the group with acne relative to those without acne approached significance (FIG. 4, p=0.088) prior to any interventions. The levels of TNF-alpha were not significantly different in those with and without acne.

Figure 5:
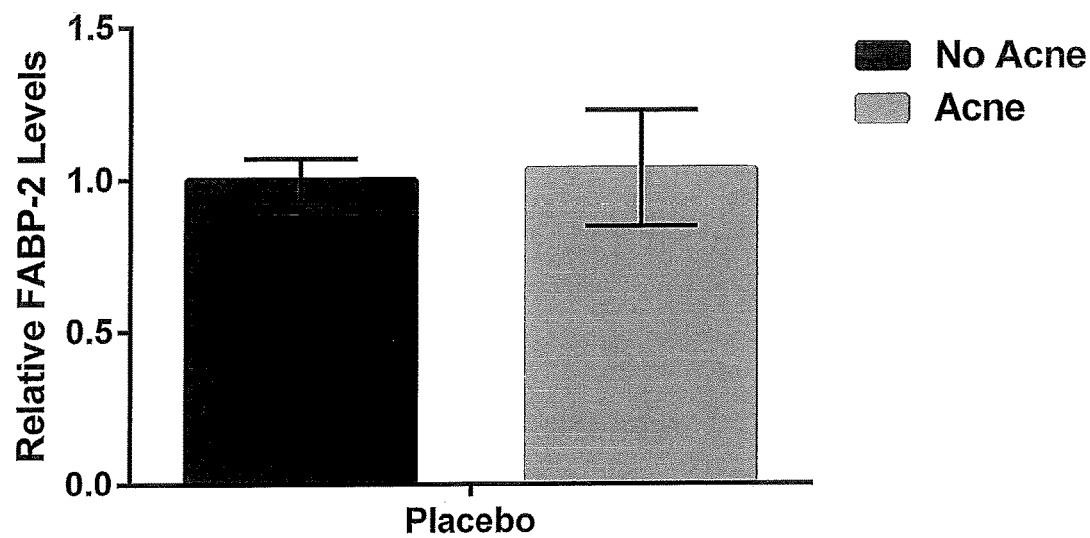
FIG. 5 depicts FABP-2 levels. Participants in both groups were given placebo for the first four weeks followed by four weeks of probiotics. (A) Relative FABP-2 concentration at the end of placebo treatment in the acne and no acne group were not significantly different. (B) There was a trend toward a decrease in FABP-2 after the probiotic exposure in the acne group. Error bars represent Mean+SEM, *p=<0.05.
Figure 5:
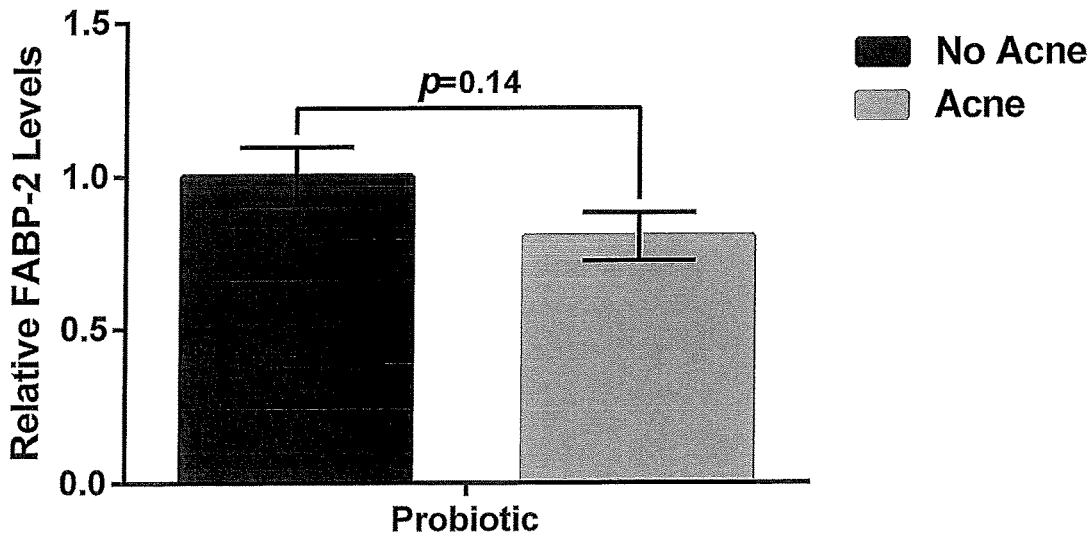
Figure 6:
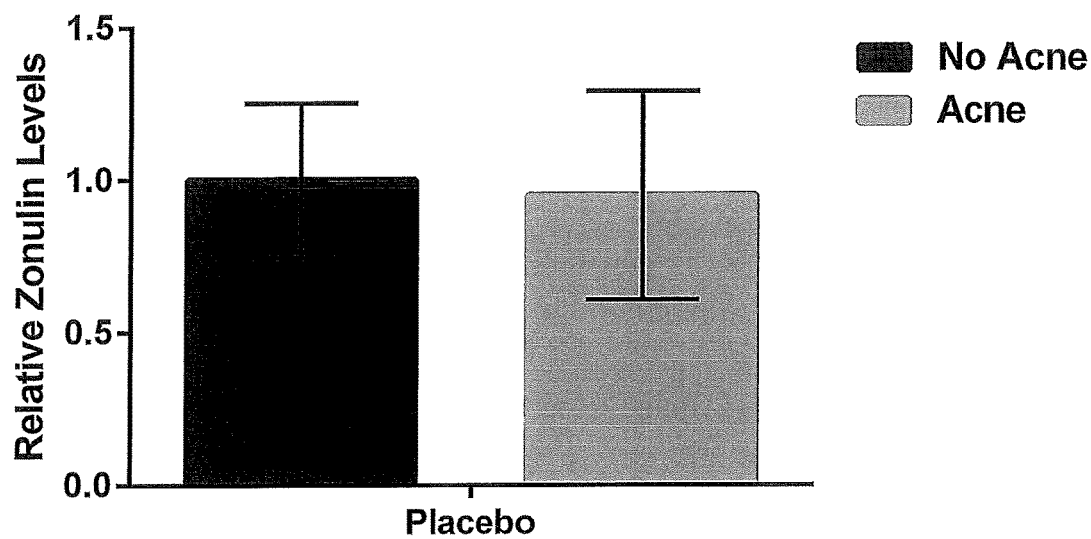
FIG. 6 depicts Zonulin levels. Participants in both groups were given placebo for the first four weeks followed by four weeks of probiotics. (A) Relative zonulin concentrations at the end of placebo treatment in the acne and no acne group were not significantly different. (B) Relative zonulin concentrations at the end of the probiotic treatment were trending toward an increase in the acne group. Error bars represent Mean+SEM, *p=<0.05.
Figure 6:
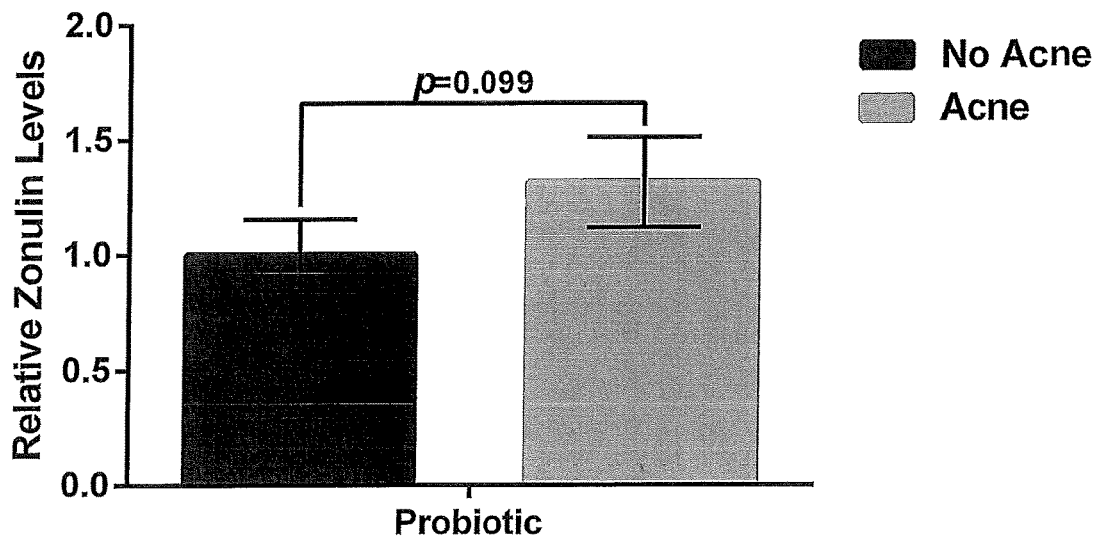
Figure 7:
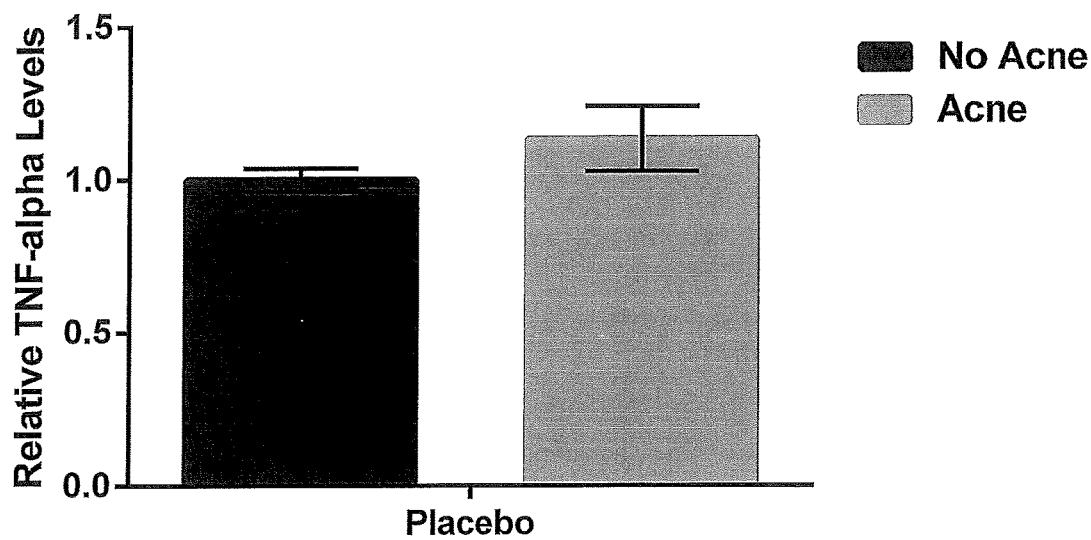
FIG. 7 depicts TNF-alpha levels. Participants in both groups were given placebo for the first four weeks followed by four weeks of probiotics. (A) Relative TNF-alpha concentrations at the end of placebo treatment in the acne and no acne group were not significantly different. (B) Relative TNF-alpha concentrations at the end of probiotic treatment in the acne and no acne group were not significantly different. Error bars represent Mean+SEM, *p=<0.05.
Figure 7:
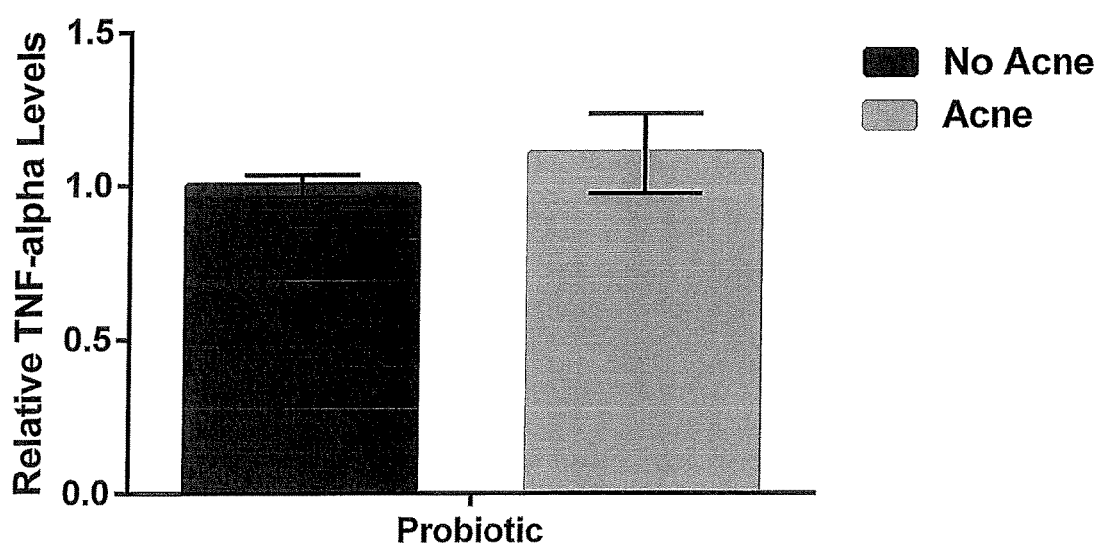
Figure 8:
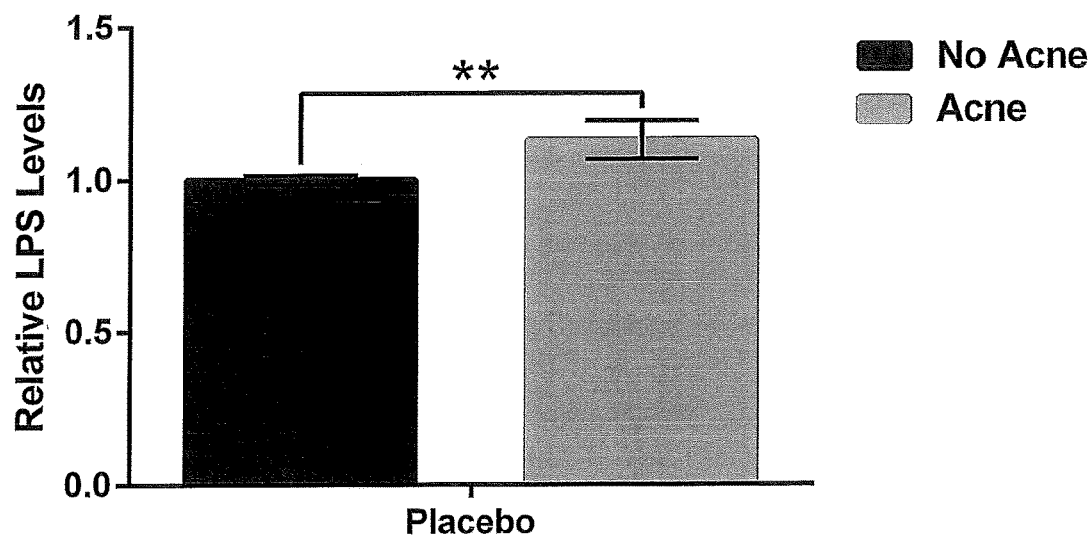
FIG. 8 depicts LPS levels. Participants in both groups were given placebo for the first four weeks followed by four weeks of probiotics. (A) Relative LPS concentrations at the end of placebo treatment in the acne group were significantly increased but not in the no acne group. (B) Relative LPS concentrations at the end of probiotic treatment in the acne and no acne group were not significantly different. Error bars represent Mean+SEM, *p=<0.05.
Figure 8:
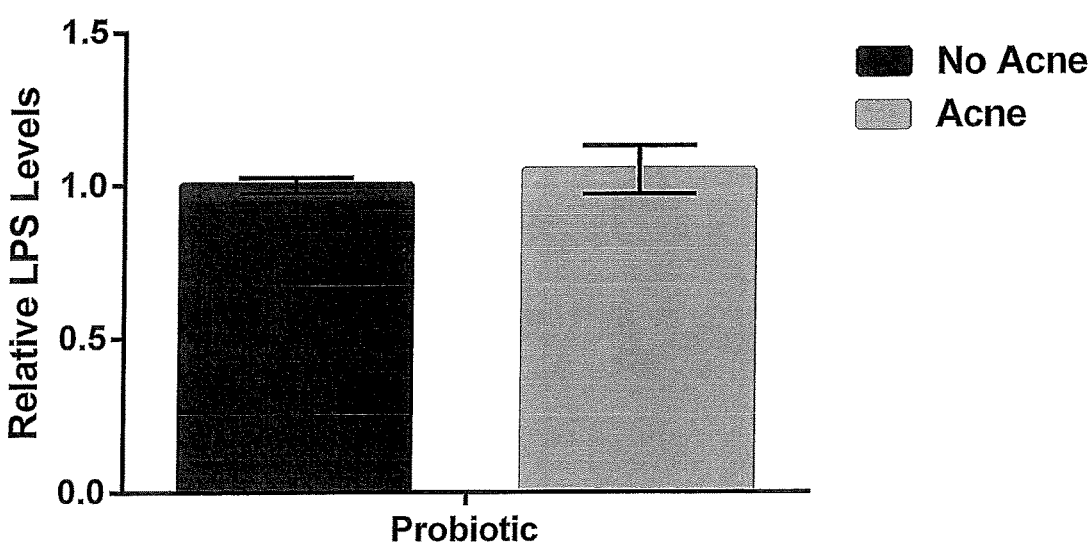

Intervention with placebo led to no change in FABP-2 (FIG. 5), Zonulin (FIG. 6) or in TNF-alpha (FIG. 8). The LPS level significantly increased in those with acne during the placebo exposure but not in the group without acne (FIG. 8, p<0.05). Exposure to the probiotic led to normalization of LPS (FIG. 8) while the levels of zonulin and TNF-alpha remained unchanged. There a decrease in FABP-2 levels (p=0.14) and an increasing trend in the zonulin levels (p=0.099) after probiotic exposure.

Acne Response to Probiotic Intervention

Figure 9:
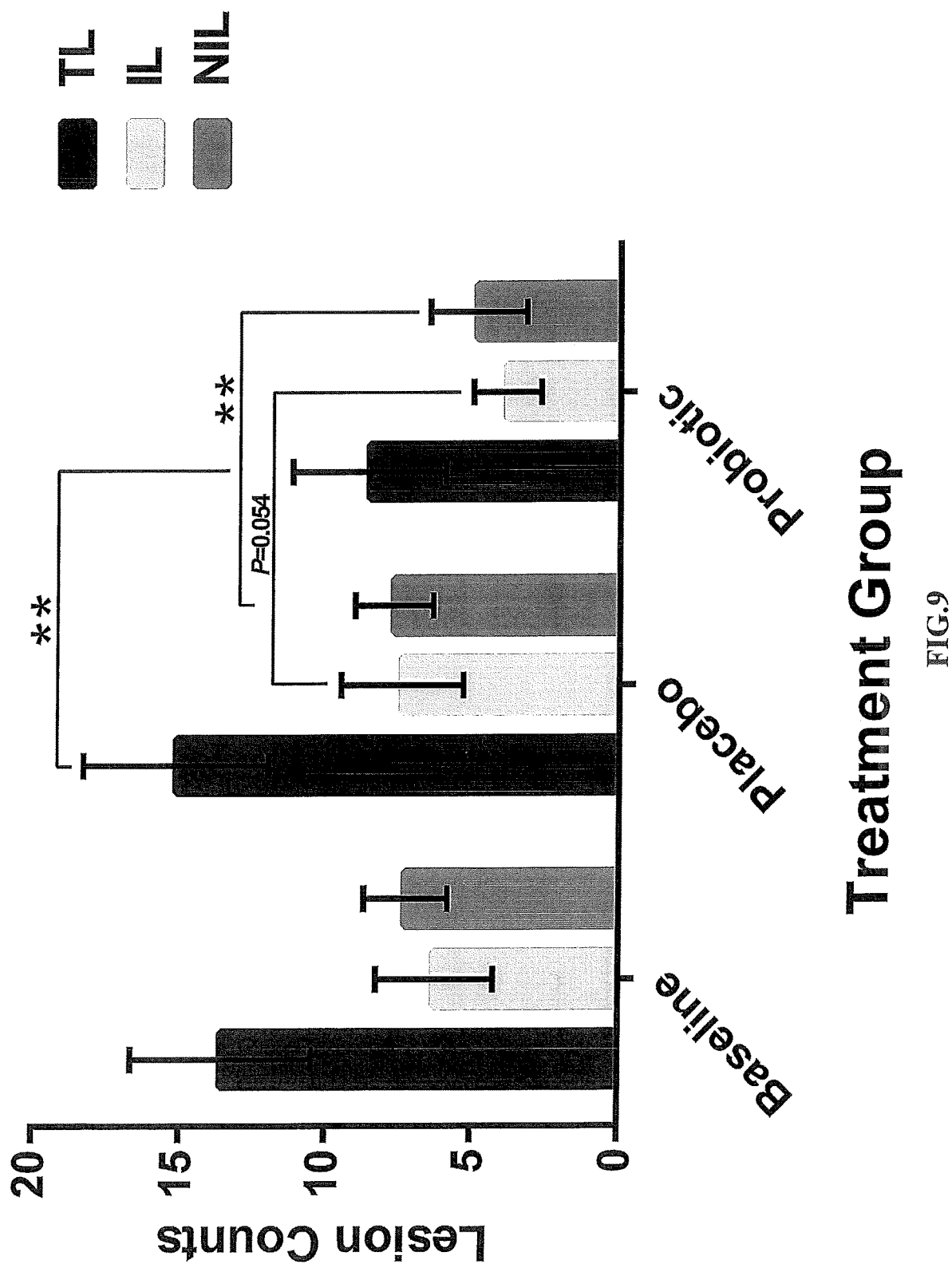
FIG. 9 depicts acne lesion counting. Acne lesions were counted at each visit in the participants with non-cystic acne (n=7). There was no change in acne lesions counts after exposure to placebo. However, probiotic supplementation lead to significant decreases in the total lesion (TL) and non-inflammatory lesion (NIL) counts. The inflammatory lesion (IL) trended toward a decrease (p=0.054). Error bars represent Mean+SEM, *p=<0.05, **p=<0.01.

At the end of the study, to further investigate the sebum related changes, evaluated the photographs of those with acne were evaluated for changes in their acne severity. There was no change in the lesion counts after the placebo intervention. However, total lesion counts and the non-inflammatory lesion counts significantly decreased after 4 weeks on the probiotic (FIG. 9). The decreasing inflammatory lesion count approached significance after probiotic exposure (p=0.054). Overall, the results show that objective measures of acne improved after 4 weeks of probiotics.

Changes in the Gut and Skin Microbiome

We first assessed for global changes in the overall diversity of the gut and the skin microbiome. Neither the gut nor the skin microbiome Shannon diversity shifted after the placebo or probiotic interventions.

When evaluating the gut microbiome and stratifying by subjects with and without acne, there were several patterns that emerged although the overall diversity did not shift.

In the control (non-acne) group, the fecal bacterial genus with the largest bacterial changes after 4 weeks on the probiotic included *Alloprevotella* (42-fold increase), *Lactococcus* (17.8-fold increase), Rhodospirillales (11.1-fold increase), and *Prevotella* (9.7-fold increase). The largest relative abundance changes were in *Akkermansia* (2.8-fold increase), *Prevotellacae* NK3B31 group (2.9-fold increase), *Lactobacillus* (13-fold decrease), [*Ruminococcus*] *torques* group (3.5-fold decrease), and *Streptococcus* (11.6-fold decrease).

Subanalysis of the acne group showed that the fecal bacterial genus with the largest bacterial changes after 4 weeks on the probiotic included Selenomonadales (16-fold increase), [*Ruminococcus*] *gnavus* group (14.9-fold increase), Erysipelatodostridium (12.5-fold increase), Ruminidostridium (7-fold decrease), Erysipelotrichaceae (9-fold decrease) *Butyricoccus* (8.6-fold decrease), *Ruminiococcus* (10-fold decrease), and *Clostridium sensu stricto* (33.8-fold decrease). The largest relative abundance changes were in *Streptococcus* (6.2-fold increase), [*Ruminococcus*] *gnavus* group (14.8-fold increase), *Veilonella* (5.3-fold decrease).

Changes in the Blood Short Chain Fatty Acids

At baseline, those with acne were found to have a trend toward a lower acetate levels (p=0.15) while no changes were found when comparing the blood butyrate and propionate levels (FIG. 10). After probiotic supplementation, overall there was an increasing trend in the acetate levels (FIG. 10B, p=0.13) and a significant increase in the acetate: propionate ratio. Subanalysis of the non-acne group showed increasing acetate levels approaching significance (FIG.

10D, p=0.11) and increase in the acetate:propionate ratio (p=0.05). Subanalysis of the acne group showed a 2.6-fold increase in the acetate:propionate ratio but this difference was not statistically significant (p=0.33).

Discussion

The study shows that oral supplementation with probiotics may influence the skin's sebum level and its biophysical properties. While a gut-skin axis has long been explored in many different traditions such as Ayurvedic medicine and Traditional Chinese medicine, this work extends the growing body of literature that suggest clinical evidence for such a connection.

An unexpected finding was that the sebum trends noted in the overall recruited participants was more likely due to shifts within the participants that had non-cystic acne. Studies in acne improvement are typically carried out over 8 to 12 weeks. However, even over four weeks a 37% decrease was noted in the total lesion count, which is in agreement with the other published probiotic study for acne where the authors showed a 38% decrease in acne after four weeks (Jung G. W., et al., 2013). Therefore, the findings here of improvements in the total lesion count, non-inflammatory lesion count, and the inflammatory lesion count coupled with the tendency for a decrease in sebum production suggest modulation of acne via modulation of sebum production. While the mechanism for the shift in sebum is not clear, a future study is warranted. While the recruitment population was restricted to non-cystic acne, future studies should consider recruitment and assessment in those with more advanced acne. One advantage of this study is that we utilized a placebo group and each person served as their own control to better isolate the effects of the probiotic and to decrease inter-individual variation.

There were several lines of evidence of "leaky gut" noted here. When assessing LPS, there were no overall changes before and after probiotic supplementation. However, LPS was increased within the acne subpopulation with exposure to placebo and this normalized with exposure to probiotics. The FABP-2 marker was elevated in those with acne at baseline which normalized during placebo exposure and had a reducing trend with probiotic exposure within the acne subgroup. Although FABP-2 has been reported as a marker of gut permeability, it is also involved in fatty acid transport and lipid absorption and high fat diets may increase the levels of FABP-2. Therefore the tendency for elevation in FABP-2 levels at baseline in those with acne may represent a higher fat intake or a greater sensitivity to fat at the gut level. Regardless, there was a trend toward reducing the FABP-2 levels after probiotic supplementation, suggesting that the probiotics may have a normalizing trend in FABP-2 in those with acne, and this correlated with a decrease in sebum production and with an improvement in clinical acne. Taken together, the results suggest that there may be evidence for "leaky gut" with changes in LPS and FABP-2 in those with acne with early evidence for correction with probiotic exposure. However, further assessments of the role of LPS and FABP-2 are necessary and warranted in a larger study for further evaluation.

Several interesting shifts in the microbiome were noted. Firstly, the skin microbiome nor the gut microbiome diversity did not shift although there were still several shifts in individual bacteria that are worth noting. The probiotic used in this study (*Bacillus* species) is composed of spore-forming bacteria that typically are abundant in the small intestine. The sampling method was focused on fecal collection that are more abundant in colonic and rectal organisms and may not reflect changes in diversity at the level of the small intestines.

When assessing individual bacteria, there were several notable findings. In the non-acne population, probiotic supplementation lead to an increase in the presence of *Akkermansia*, and this is in agreement with previous supplementation studies with *Bacillus* based probiotics. We also noted that the abundance of the *Lactococcus* and *Prevotella* species increased in the non-acne group. *Lactococcus* has been reported to have anti-inflammatory effects while *Prevotella* has been purported as a bacterium associated with a non-western diet that is higher in complex fibers. Both *Akkermansia* and *Prevotella* are known to produce short chain fatty acids33 which was reflected in the increasing trend in the blood acetate levels and the acetate:propionate ratio after probiotic supplementation.

In the subanalysis of the participants with acne, probiotic supplementation led to an increase in the presence of the Lachnospiraceae and [*Ruminococcus*] *gnavus* group and a decrease in the *Butyricicoccus* species. [*Ruminococcus*] *gnavus* is part of the Lachnospiraceae family of bacteria and short chain fatty acid producing bacteria, especially propionate, that may have anti-inflammatory effects. A trend was noted for a relative decrease in the blood levels of the acetate short chain fatty acid in those with acne. Although it was not statistically significant, it was notable that the acetate:propionate levels had increased after probiotic supplementation overall and in the non-acne group. The acne group had a large effect size with a 2.6 fold increase but without reaching statistical significance. Because the acne subanalysis is underpowered, the findings warrant further study with a larger cohort. Future studies should involve an expanded population that is focused on participants with acne to assess how their lipidome and microbiome shift with probiotic supplementation. It remains unclear how the gut may communicate with the skin in those with acne but short chain fatty acids remain as a candidate deserving of further scrutiny.

When considering the skin biophysical changes, it is notable that skin hydration did not change but the TEWL increased after probiotic supplementation. This correlated with a trend toward a decrease in sebum production and it may reflect that sebum is a contributor to reducing TEWL. There were no instances of dry or irritated skin that was noticed as a complaint or objectively noted among the participants.

There are several limitations to this study. This study was focused on a relative low number of subjects with acne and future studies will need to expand the acne cohort. However, this study did rely on objective measures such as the total lesion count and was corroborative with previous observations of probiotics with acne (Jung G. W., et al., 2013). Furthermore, the lesion counts were associated with a decreasing trend in sebum production and lends further support for the observations. A second limitation is that the fecal collections were more representative of the distal colonic microbiome rather than a true representation of the entire gut. This is a common limitation in most gut microbiome analyses but this study included evaluations of blood levels of gut derived markers and short chain fatty acids, which allows for assessment of global influences of the gut beyond assessment of just the gut microbiome. A third limitation is that the intervention was one over only 4 weeks. However, participants first underwent a washout with the placebo prior to shifting to probiotic supplementation and each person served as their own control and this boosted the overall statistical power of the study. Future studies, especially with acne, should be extended for 8 or 12 weeks. Finally, the study did not institute any washouts or guidelines for diet for the participants and the study results could have been influenced by diet as this can also affect the gut microbiome and the production of short chain fatty acids. However, the study utilized each person as their own control, which controls for the influence of diet and strengthens the present findings.

Overall, it was found that probiotic supplementation shifted the skin's biophysical properties with a trend to decrease sebum production, especially among those with acne. Subgroup analysis of those with acne showed that total, non-inflammatory, and inflammatory lesion counts were improved. The non-acne population had an increase in the *Akkermansia* while the acne population had an increase in the Lachnospiraceae and [*Ruminococcus*] gnavus. While this study warrants more research interest in probiotics, future studies will be needed to better delineate the role of probiotics in sebum production and in modulating acne.

Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entireties for all purposes.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The present invention may be embodied in other specific forms without departing from the spirit or essential attributes thereof, and, accordingly, reference should be made to the appended claims, rather than to the foregoing specification, as indicating the scope of the invention.

We claim:

1. A spore-based probiotic composition comprising strains *Bacillus indicus* (HU36), *Bacillus subtilis* (HU58), *Bacillus coagulans* (SC-208), and *Bacillus clausii* (SC-109), each strain comprising *Bacillus* spores.

2. The composition of claim 1, wherein said composition is a dietary supplement.

3. The composition of claim 1, wherein said spores are microencapsulated.

4. The composition of claim 1, further comprising endosomes.

5. A method of modulating dermal and sub-dermal properties of a human subject in need thereof, comprising the steps of:
   a. identifying the human subject in need of dermal or sub-dermal modulation;
   b. administering to the human subject an effective amount of the spore-based probiotic composition of claim 1.

6. The method of claim 5, wherein one or more of acetate, propionate, or butyrate is increased in the human gastro-intestinal tract.

7. The method of claim 6, wherein the ratio of acetate to propionate or butyrate is substantially increased in the human gastro-intestinal tract.

8. The method of claim 5, wherein the spore-based probiotic composition is administered in a daily dose of about $1\times10^8$ to about $1\times10^{12}$ *Bacillus* spores (CFUs).

9. The method of claim 8, wherein the spore-based probiotic composition is administered in a daily dose of about $4\times10^9$ *Bacillus* spores (CFUs).

10. The method of claim 5, wherein said modulated properties are one or more of increased skin hydration, reduced wrinkly appearance, reduced sebum content, reduced skin inflammation, improved lipidome on the skin, improved skin microbiota, and reduced appearance and/or frequency of acne lesions or rosacea.

11. The method of claim 5, wherein said administering step is by oral administration.

12. A method of reducing the appearance and/or frequency of acne lesions of a human subject in need thereof, comprising the steps of:
   a. identifying the human subject in need of dermal or sub-dermal modulation;
   b. administering to the human subject an effective amount of the spore-based probiotic composition of claim 1.

13. The method of claim 12, wherein one or more of acetate, propionate, or butyrate is increased in the human gastro-intestinal tract.

14. The method of claim 13, wherein the ratio of acetate to propionate or butyrate is substantially increased in the human gastro-intestinal tract.

15. The method of claim 12, wherein the spore-based probiotic composition is administered in a daily dose of about $1\times10^8$ to about $1\times10^{12}$ *Bacillus* spores (CFUs).

16. The method of claim 15, wherein the spore-based probiotic composition is administered in a daily dose of about $4\times10^9$ *Bacillus* spores (CFUs).

17. The method of claim 12, wherein said appearance and/or frequency of acne lesions are one or more of increased skin hydration, reduced wrinkly appearance, reduced sebum content, reduced skin inflammation, improved lipidome on the skin, improved skin microbiota, and reduced appearance and/or frequency of acne lesions.

18. The method of claim 12, wherein said administering step is by oral administration.

* * * * *